United States Patent
Bolckmans et al.

(10) Patent No.: US 9,781,937 B2
(45) Date of Patent: Oct. 10, 2017

(54) MITE COMPOSITION COMPRISING A PREDATORY MITE AND IMMOBILIZED PREY CONTACTED WITH A FUNGUS REDUCING AGENT AND METHODS AND USES RELATED TO THE USE OF SAID COMPOSITION

(71) Applicant: Koppert B.V., Berkel en Rodenrijs (NL)

(72) Inventors: Karel Jozef Florent Bolckmans, Hoogstraten (BE); Yvonne Maria Van Houten, Naaldwijk (NL); Adelmar Emmanuel Van Baal, Delft (NL); Radbout Timmer, The Hague (NL); Damien Marc Morel, Nantes (FR)

(73) Assignee: Koppert B.V., Berkel en Rodenrijs (NL)

( * ) Notice: Subject to any disclaimer, the term of this patent is extended or adjusted under 35 U.S.C. 154(b) by 0 days.

(21) Appl. No.: 14/370,624

(22) PCT Filed: Oct. 23, 2012

(86) PCT No.: PCT/NL2012/050736
§ 371 (c)(1),
(2) Date: Jul. 3, 2014

(87) PCT Pub. No.: WO2013/103294
PCT Pub. Date: Jul. 11, 2013

(65) Prior Publication Data
US 2015/0128864 A1 May 14, 2015

Related U.S. Application Data

(60) Provisional application No. 61/583,152, filed on Jan. 4, 2012.

(51) Int. Cl.
*A01N 63/00* (2006.01)
*A01K 67/033* (2006.01)

(52) U.S. Cl.
CPC ............ *A01N 63/00* (2013.01); *A01K 67/033* (2013.01)

(58) Field of Classification Search
CPC ............................. A01N 63/00; A01N 67/033
(Continued)

(56) References Cited

U.S. PATENT DOCUMENTS

| 4,646,683 A | 3/1987 | Maedgen, Jr. |
| 5,192,546 A | 3/1993 | Abercrombie |

(Continued)

FOREIGN PATENT DOCUMENTS

| CN | 1440646 A | 9/2003 |
| CN | 101040612 A | 9/2007 |

(Continued)

OTHER PUBLICATIONS

Amin et al., "Response of the Predatory Mite Phytoseiulus macropilis (Acari: Phytoseiidae) to Pesticides and Kairomones of Three Spider Mite Species (Acari: Tetranychidae), and Non-Prey Food", Florida Entomologist (2009), 92(4):554-562.
(Continued)

*Primary Examiner* — Joshua Huson
(74) *Attorney, Agent, or Firm* — Bret E. Field; Bozicevic, Field & Francis LLP

(57) ABSTRACT

The present invention in general relates to the field of biological crop protection by use of predatory mites. More particularly the present invention relates to a mite composition comprising a predatory mite and a prey. Such a mite composition is suitable for rearing the predatory mite and/or for crop protection using the predatory mite. The prey in the composition comprises individuals of at least one *Astigma-*
(Continued)

Figure 1:
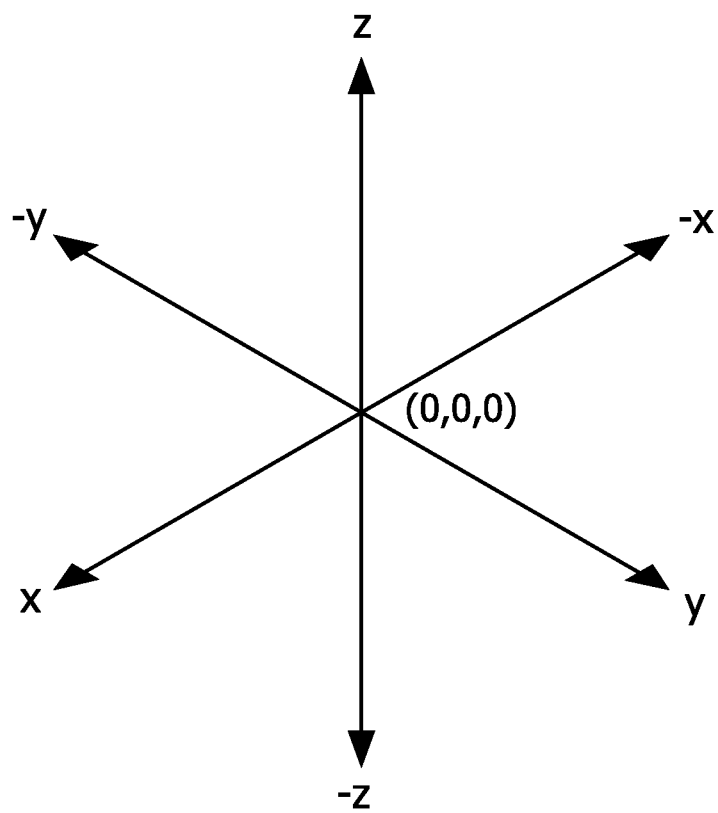

Means: 883 (live), 1325 (live+frozen); p= 0,011 tid mite species, wherein at least a fraction of the *Astigmatid* individuals is immobilized. The composition is characterized in that immobilized *Astigmatid* individuals are contacted with a fungus reducing agent.

20 Claims, 8 Drawing Sheets

(58) Field of Classification Search
USPC .......................... 119/6.5, 6.6; 424/538, 93.1
See application file for complete search history.

(56) References Cited

U.S. PATENT DOCUMENTS

| | | | |
|---|---|---|---|
| 6,129,935 | A | 10/2000 | White et al. |
| 8,097,248 | B2 | 1/2012 | Bolckmans et al. |
| 2003/0091657 | A1* | 5/2003 | Chiasson ....................... 424/725 |
| 2005/0042244 | A1 | 2/2005 | Hino et al. |
| 2005/0178337 | A1 | 8/2005 | Wright |
| 2009/0036547 | A1* | 2/2009 | Shah et al. ..................... 514/764 |
| 2009/0099135 | A1* | 4/2009 | Enan ................................. 514/86 |
| 2010/0056620 | A1* | 3/2010 | Fischer et al. ................ 514/462 |
| 2010/0119645 | A1* | 5/2010 | Fidgett et al. .................... 426/2 |
| 2010/0316738 | A1* | 12/2010 | Jimenez et al. .............. 424/725 |

FOREIGN PATENT DOCUMENTS

| | | |
|---|---|---|
| EP | 0777963 | 6/1997 |
| EP | 2232986 A2 | 9/2010 |
| EP | 2380436 A1 | 10/2011 |
| GB | 2168680 | 6/1986 |
| GB | 2393890 A | 4/2004 |
| JP | 03108433 | 5/1991 |
| JP | 8-40814 A | 2/1996 |
| JP | 2009-522256 A | 6/2009 |
| JP | 2011-121958 A | 6/2011 |
| WO | WO 97/34468 | 9/1997 |
| WO | WO 99/59402 | 11/1999 |
| WO | WO 2006/057552 A1 | 6/2006 |
| WO | WO 2006/071107 A1 | 7/2006 |
| WO | WO 2007/075081 | 7/2007 |
| WO | WO2007075081 A1 | 7/2007 |
| WO | WO 2008/015393 A2 | 2/2008 |
| WO | WO 2008/104807 A2 | 9/2008 |
| WO | WO 2013/043050 A1 | 3/2013 |

OTHER PUBLICATIONS

Cross et al., "Effects of repeated foliar sprays of insecticides or gungicides on organophosphate-resistant strains of the orchard predatory mite Typhlodromus pyri on apple", Crop Protection (1994), 13(1):39-44.

Cuthbertson et al., "The impact of fungicides to control apple scab (Venturia inaequalis) on the predatory mite Anystis baccarum and its prey Aculus schlechtendali (apple rust mite) in Northern Ireland Bramley orchards", Crop Protection (2003), 22(9):1125-1130.

Schmidt et al., "Felduntersuchungen zur Wirkung von Euparen Multi and Euparen auf das System Spinnmilbe-Raubmilbe", Pflanzenschutz-Nachrichten Bayer (1998), 51(1):37-50.

Abou-Awad et al., "Environmental management and biological aspects of the two eriophyoid fig mites aceria ficus (cotte) and rhyncaphytoptus ficifoliae Keifer in Egypt", Anz. Schädlingskunde / J. Pest Science (2000), 73:5-12.

Abou-Awad et al., "Impact of two eriophyoid fig mites, aceria ficus and rhyncaphytoptus ficifoliae, as prey on postembryonic development and oviposition rate of the predacious mite amblyseius swirskii", Acarologia (1999), 40(4):367-371.

Abou-Awad, "Effects of Artificial and Natural Diets on the Development and Reproduction of Two Phytoseiid Mites Amblyseius Gossipi and Amblyseius Swirskii (Acari: Phytoseiidae)", Insect Sci Applic (1992), 13(3):441-445.

Arthur et al. Irradiation as a phytosanitary treatment for mites of the species Tyrophagus putrescentiae (ACARI : ACARIDAE), 2009 International Nuclear Atlantic Conference—INAC 2009 Rio de Janeiro, RJ, Brazil, Sep. 27 to Oct. 2, 2009, 6 pages.

Barajas et al. "Effect of temperature on the drying process of bee pollen from two zones of colombia", Journal of Food Process Engineering 35 (2012) 134-148.

Baxter et al. Field results of a sachet re-lease system using the predator Amblyseius swirskii (Athias-Henriot) (Acari: Phytoseiidae) and the factitious prey, Suidasia medanensis Oudemans (Acari: Astigmata), Integrated control in protected crops, temperate climate IOBC/wprs Bulletin vol. 68, 2011, pp. 1-4.

Beglyarov et al., "The flour mite [Acarus siro] for mass breeding of phytoseiids", Zashchita-Rastenii (1990), No. 10, pp. 25.

Bennison et al., "Integrated control of Frankliniella occidentalis (Pergande) in UK cucumber crops-evaluation of a controlled release system of introducing Amblyseius cucumeris." Med. Fac. Landbouww. Rijksuniv. Gent (1991), 56(2A):251-258.

Bennison et al., "Recent developments with integrated control of thrips on cucumber in the United Kingdom", International Organisation for Biological and Integrated Control of noxious animals and plants, Glasshouse pests SROP/WPRS Bull (1990), 13(5):19-26.

Bermudez et al. Effect of Pollen from Different Plant Species on Development of Typhlodromus pyri (Sheuten) (Acari: Phytoseiidae), Chilean Journal of Agricultural Research 70(3):408-416 (Jul.-Sep. 2010).

Castagnoli et al., "Short-term changes in consumption and oviposition rates of Neoseilus californicus strains (Acari: Phytodeiidae) after a diet shift", Experimental and Applied Acarology (2001), 25(12):969-983.

Castagnoli et al., "Effect of long-term feeding history on functional and numerical responses of Neoseiulus californicus (Acari: Phytoseiidae)", Experimental and Applied Acarology (1999), 23:217-234.

Cebolla et al. Prey range of the predatory mite Cheyletus malaccensis (Acari: Cheyletidae) and its efficacy in the control of seven stored-product pests, Biological Control, vol. 50, pp. 1-6 (2009).

Chant et al., "A review of the subfamily Amblyseiinae Muma (Acari: Phytoseiidae) Part I. Neoseiulini new tribe" International Journal of Acarology (2003), 29:3-46.

Chant et al., "A review of the subfamily Amblyseiinae Muma (Acari: Phytoseiidae) Part III. The tribe Amblyseiini Wainstein, subtribe Amblyseiina N. Subtribe" International Journal of Acarology (2004), 30:171-228.

Chmielewski, Acceptance of buckwheat grain as a food by Tyrophagus putrescentiae (Schr.) (Acari. Acaridae), Fagopyrum 16, pp. 95-97 (1999).

Chmielewski, "Bionomics of Carpoglyphus lactis (Acari: Carpoglyphidae) on honey", In Bruin et al. (eds.) Ecology and Evolution of Acari (1999), 423-424.

Chmielewski, "Morfologia, biologia I ekologia Carpoglyphus lactis (L. 1758) (Glycyphagidae, Acarina)", Prace Nauk. Inst. Ochrony Roslin 13 (1971), 13(2):63-166.

Chmielewski, "Wyniki badan morfologicznych, biologicznych I ekologicznych nad rortoczkiem suszowym—Carpoglyphus lactis", Prace Nauk. Inst. Ochrony Roslin (1971), 13(1):87-106.

Cole et al. "Antifungal Properties of the Insect Alarm Pheromones, Citral, 2-Heptanone, and 4-Methyl-3-Heptanone", Mycologia, vol. 67, No. 4, pp. 701-708 (1975).

Collins, D. A. "A review on the factors affecting mite growth in stored grain commodities", Exp Appl Acarol, vol. 56, pp. 191-208 (2012).

Colloff, Matthew J. "Dust Mites", Co-published by Springer Science + Business Media B.V., Dordrecht, The Netherlands and CSIRO Publishing, Collingwood, Australia, 2009, pp. 65-68.

Colloff, Matthew J. "Dust Mites", Co-published by Springer Science and Business Media B.V., Dordrecht, The Netherlands and CSIRO Publishing, Collingwood, Australia, 2009, pp. 98-100.

Conjin et al., "Biological control of the bulb mite, Rhizoglyphus robini by the predatory mite Hypoaspis aculeifer on lilies: Implementation in practice", Acta Horticluturae (1997), 430:619-624.

(56) References Cited

OTHER PUBLICATIONS

Croft et al., "Do literature records of predation reflect food specializaton and predation types among phytoseiid mite (Acari: Phytoseiidae)?", Experimental & Applied Acarology (1998), 22:467-480.
Cunnington, A. M. "Physical Limits for Complete Development of the Copra Mite, Tyrophagus putrescentiae (Schrank) (Acarina, Acaridae)", Proceedings of the 2nd International Congress of Acarology, 1967, 2 pages.
Ehara, "Illustrations of the mites and ticks of Japan", Zenkoku Noson Kyoiku Kyokai, 389 and 505-509, 1st Ed. Published on Oct. 30, 1980.
El-Halawany, "Mites Inhabiting Date Palms", Plant Portection Research Institute (2000), Dokki, Egypt, pp. 366-371.
El-Laithy et al, "Life table parameters of the two phytoseiid predators, Amblyseius scutalis (Athias-Henriot) and A. swirskii A.-H. (Acari, Phytoseiidae) in Egypt", J. Appl. Ent. 113 pp. 8-12 Verlag Paul Parey, Hamburg und Berlin ISSN 0931-2048 (1992).
El-Sherif et al., "Laboratory studies on Developmental and Oviposition Rates of Amblyseius Swirskii A.-H. (Acari: Phytoseiidae) Fed on Tyrophagous putrescentiae (Schrank) (Acari: Acaridea)", Arab Journal of Biotechnology (1999), 2(2):121-126.
Enkegaard, "Newsletter on biological control in greenhouses—several articles (New phytoseiid predators)", Sting vol. 26, Danish Institute of Agricultural Sciences (2004).
Enkegaard, "Proceedings of the Working Groups Meeting", at Victoria (British Columbia, Canada), May 6-9, 2002. vol. 25(1).
Ferragut et al., "Influence of food and temperature on development and oviposition of Euseius stipulatus and Typhlodromus phialatus (Acari: Phytoseiidae)", Experimental & Applied Acarology (1987), 3(4):317-329.
Franz et al. "Mite fauna of German farms", Allergy, vol. 52, pp. 1233-1237 (1997).
Franzolin et al. "Interaction between toxigenic Aspergillus flavus Link and mites (Tyrophagus putrescentiae Schrank) on maize grains: effects on fungal growth and aflatoxin production", Journal of Stored Products Research 35 (1999) 215-224.
Galun et al., "Meeting—The 10th conference of the entomological society of Israël—Agricultural Entomology (several articles) ARO" —The volcani Center, Bet. Dagan, Israel; pp. 27 (1997).
Gerling et al., "Biological control of Bemisia tabaci using predators and parasitoids", Crop Protection (2001), 20:779-799.
Gerson et al., "Acarine Biocontrol Agents—An Illustrated Key and Manual", Chapman and Hall London, pp. 24-35 (1990).
Gerson et al., "Mites (Acari) for Pest Control", Blackwell Science, Department of Entomology, Faculty of Agricultural Food and Environmental Sciences, Hebrew University, Rehovot, Israel / Systematic Entomology Laboratory, US Department of Agriculture, Agricultural Research Service, Beltsville, MD, USA Ingediend in KR dos 12: pp. 151-158 (2003), Chapter 21.
Gerson et al., "Mites (Acari) for Pest Control", Blackwell Science, Department of Entomology, Faculty of Agricultural Food and Environmental Sciences, Hebrew university, Rehovot, Israel / Systematic Entomology Laboratory, US Department of Agriculture, Agricultural Research Service, Beltsville, MD, USA pp. 73-218 (2003), Chapter 26.
Gilkeson, "Advances in insect rearing for research and pest management", Anderson, T.E. & Leppla, N.C. (Eds). pp. 489-506 (1982).
Gilkeson, "Mass rearing of phytoseiid mites for testing and commercial application", Anderson, T.E. & Leppla, N.C. (eds.), Advances in insect rearing for research and pest management. Boulder, Colorado, Westview Press. pp. 489-506 (1992).
Greatrex, R. M. "Typhlodromus montdorensis for control of thrips in protected crops", 2nd Conference on Pherormones, Food Lure, Traps and Biological Control: Alternatives for the 21st Century; Murcia, Spain, Nov. 18-19, 2009, 5 pages.
Griffiths et al. "A survey of mites in bulk grain stored on farms in England and Wales", Proc. Assoc. Appl. Biol., vol. 82, pp. 180-185 (1976).
Griffiths et al. "Grain Storage Fungi Associated with Mites", Journal of Economic Entomology, vol. 52, No. 3, pp. 514-518 (1969).
Griffiths, "A revision of the genus Acarus L., 1758 (Acaridae, Acarina)", Bull Brit. Mus. (nat. Hist.) (Zool), (1964), 11:413-464.
Griffiths, "Some field habitats of mites of stored food products", Ann. Appl. Biol. (1960), 48:134-144.
Griffiths, D. A. "Chapter 15: Biological Control of Mites", Published in Integrated Pest and Disease Management in Greenhouse Crops, Eds. Albajes et al., Kluwer Academic Publishers, pp. 217-234 (2009).
Griffiths, D. A. "Some Field Habitats of Mites of Stored Food Products", Annals of Applied Biology, 48: 134-144 (1960).
Grout et al. "The dietary effect of windbreak pollens on longevity and fecundity of a predacious mite Euseius addoensis addoensis (Acari: Phyto-seiidae) found in citrus orchards in South Africa", Bulletin of Entomological Research 82(03):317-320, Sep. 1992 (Abstract only).
Hansen et al. "Possibilities and limitations of the use of Amblyseius Mckenzie Sch. & Pr. for biological control of thrips (Thrips tabaci Lind.) on glasshouse crops of cucumber", Department of Zoology, Danish Research Centre for plant protection, Lynby, Denmark pp. 145-150 (1985).
Hubert et al. "Astigmatid mite growth and fungi preference (Acari: Acaridida): Comparisons in laboratory experiments", Pedobiologia, vol. 48, pp. 205-214 (2004).
Hughes, "The mites of stored food and houses", 2nd ed. Ministry of Agriculture, Fisheries and Food, Technical Bulletin No. 9. His Majesty's Stationary Office, London, 287 pages; pp. 26, 27, 41 & 43 (1976).
Hughes, "The Mites of Stored Food and Houses", Technical Bulletin 9, Ministry of Agriculture, Fisheries and Food, 1977, pp. 133-186.
Hughes, A. M. "The Mites of Stored Foods and Houses", Ministry of Agriculture, Fisheries and Food , Her Majesty's Stationery Office, London, 1976, 400 pages.
Jacobson, "Integrated pest management in cucumbers—prevention of establishment of Frankliniella occidentalis (pergande)", Med. Fac. Landbouww Univ. Gent 60/3a (1995).
Jankovic et al. The Effects of Microwave Radiation on Microbial Cultures, Hospital Pharmacology 1(2): 102-108 (2014).
Japanese Society of Applied Entomology and Zoology; Franklinielle Schultzei (Japanse titel, geen Engelse versie voorhanden); Japanese Society of Applied Entomology and Zoology NII—Electronic Library services, pp. 85 (2001).
Jarrat, "Stored-product pests", Pest-Management Principles, pp. 61-67. Publication 2247 Mississippi State University Extension Service, http://msucares.com/pubs/publications/p2247ch7.pdf (2001).
Karg et al., "Advantages of oligophagous predatory mites for biological control", Institute of plant protection Kleinmachnow, near Berlin GDR (1987).
Karg, "Die ökologische Differenzierung der Raubmilbenarten der Überfamilie Phytoseioidea Karg (Acarina, Parasitiformes) (The ecological differentiation of the predatory mite species of the superfamily Phytoseioidea Karg (acarina, Parasitiformes))", Zool. Jb. Syst. (1989), 116: 31-46 (English abstract only).
Karg, "Progress in the use of predatory mites for biological control in greenhouses. Fortschritte bei der Anwendung von Raubmilben zur biologischen Schädlingsbekämpfung in Gewächshäusern", Gartenbau: Zeitschrift fuer den Gemuesebau, Obstbau and Zierpflanzenbau der D.D.R. Voortz. Van : Deutsche Gartenbau Voortg. Als Gartenbau (1989), 36(2):44-46.
Kethley et al., "A terrestrial alicorhagiid mite (Acari: Acariformes) from the Devonian of New York", Micropaleontology (1989), 35:367-373.
Kim, "Control of Thrips Using PredAtory Mite", National Institute of Agricultural Science and Technology (2000).
Knulle, "Expression of a dispersal trait in a guild of mites colonizing transient habitats", Evolutionary Ecology (1995), 9: 341-353.
Koike et al., "Phyto-Trap", NII electronic Library Service Jpn. J. Appl. Entomol. Zool. (1999), 44:35-40.
Kozakiewicz et al. "Physiology of Aspergillus—Appendix I—Table 2", Ed. J. E. Smith, Plenum Press New York, 1994, 1 page.

(56) References Cited

OTHER PUBLICATIONS

Kozakiewicz, "Aspergillus Species on Stored Products", Mycological Papers, No. 161, Jun. 30, 1989, 3 pages.
Kuwahara et al. "Antifungal Activity of Caloglyphus polyphyllae Sex Pheromone and Other Mite Exudates", Naturwissenschaften 76, pp. 578-579 (1989).
Leal et al. "Neryl Myristate from the Acarid Mite, Aleuroglyphus ovatus (Acarina, Acaridae)", Agricultural and Biological Chemistry, vol. 52, No. 5, pp. 1299-1300 (1988).
Leal et al. "The Alarm Pheromone of the Mite Suidasia medanensis OUDEMANS, 1924 (Acariformes, Suidasiidae)", Agricultural and Biological Chemistry, vol. 53, No. 10, pp. 2703-2709 (1989).
Matsumoto et al., "The Alarm Pheromone of Grain Mites and Its Antifungal Effect", Recent Advances in Acarology, vol. 1, pp. 243-249 (1979).
McKenzie et al., "Khishchye kleshchi v zakrytom grunte (Predatory mite under cover)", Kiev, Naukova Dumka, pp. 35 / Doss 13 EA: pp. 35, 128, 136-143 (1991).
McMurtry et al., "Life-styles of phytoseiid mites and their roles in biological control", Annual Review of Entomology (1997), 42:291-321.
McMurtry et al., "Nutritional Ecology of Phytoseiid Mites", Chapter 19, Nutritional Ecology of Phytoseiid Mites, John Wiley & Sons, Inc., pp. 609-644 (1987).
Meshkov, "Guidelines for rearing and using Neoseiiulus cucumeris (formerly Amblyseius cucumeris) predatory mite against pellucid strawberry mite", Collection of guidelines for plants protection, St. Petersburg, pp. 87-92 (1998).
Messelink et al., "Bestrijding van kaswittevlieg met roofmijten in komkommer", Praktijkonderzoek Plant & Omgeving B.V. Wageningen UR; pp. 1-17 (2005).
Messelink et al., "Roofmijten bestrijden wittevlieg" Vakblad voor Bloemisterij (2004), 43:62.
Momen et al., "Biology and feeding behaviour of the predatory mite, amblyseius swirskii (Acari: Phytoseiidae)", National Research centre, plant protection department, Dokki Cairo, Egypt. Acarologia, t. XXXIV 34 fasc. 3 pp. 199-204 (1993).
Muma et al., "Phytoseiidae of Florida. Arthropods of Florida and neighbouring land areas", 6, Fla. Dept. Agr. Cons. Serv. Div. Plant Ind., Gainsville, 150 pages; p. 62, 100 (1970).
Nesvorna et al. Suitability of a range of Fusarium species to sustain populations of three stored product mite species (Acari: Astigmata), Journal of Stored Products Research, vol. 48, Jan. 2012, pp. 37-45.
Nomikou et al., "Phytoseiid predator of whitefly feeds on plant tissue", Experimental and Applied Acarology (2003), 31:27-36.
Nomikou et al., "Phytoseiid predators as potential biological control agents for Bemisia tabaci", Exp. Appl. Acarol. (2001), 25:271-291.
Nomikou et al., "Phytoseiid predators of whiteflies fed and reproduce on non-prey food sources", Exp. Appl. Acarol. (2003), 31:15-26.
Nomikou et al., "Phytoseiid predators suppress populations of Bemisia tabaci on cucumber plants with alternative food", Experimental and Applied Acarology (2002), 27:57-68.
Norton et al., "Oribatid mite fossils from a terrestrial Devonian deposit near Gilboa, New York", Journal of Paleontology (1988), 62:259-269.
O'Connor, B. M. "A Manual of Acarology—Chapter 16: Cohort Astigmatina", Ed. Krantz et al., 3rd Edition, Texas Tech University Press, 2009, pp. 565.
Okabe et al. "A method for both mass and individual rearing of fungivorous astigmatid mites (Acari)", Experimental and Applied Acarology (2001) 25: 493-504.
Okamoto et al. "Studies on antifungal effect of mite alarm pheromone Citral, Evaluation of antifungal effect of Citral," Japanese Journal of Sanitary Zoology, vol. 29, No. 3, pp. 255-260 (1978).
Oudemans, "10.4.2 Neosiulus cucumeris" Mites of Greenhouses Part III Beneficial Mites, Chapter 10 Phytoseiid Mites ; pp. 186-189 (2003).
Overmeer, "2.1.3.2. Alternative Prey and other food resources", Alternative prey and other food resources, p. 131-137. In Helle W, Sabelis MW, Spider mites, their biology, natural enemies and control vol. 1B. In Helle W, Sabel MW, Spider mites, Their biology, natural enemies and control vol. 1B. Amsterdam, Elsevier Science Publishers BV, Amsterdam (1995).
Palevsky et al., "Identification and evaluation of potential predators of the citrus rust mite, phyllocoptruta oleivora, in Israël", Systematic and Applied Acarology (2003), 8:39-48.
Parkinson et al. "Longevity and fecundity of Acarus siro on four field and eight storage fungi", Experimental & Applied Acarology, Apr. 1991, vol. 11, Issue 1, pp. 1-8.
Parkinson, "Culturing free-living astigmatid mites", Adas Slough Laboratory, Ministry of Agriculture Fisheries and Food, London Road, Slough, Berhshire (1992).
Perkins, M. "Ozone in Food Processing Applications: Past Experience, Future Potential and Regulatory Issues", Zentox Corporation, Presented at ConnecTECH '97, Atlanta, GA, 6 pages (1997).
Piechnik et al., "Food-web assembly during a classic biographic study: species' "trophic breadth "corresponds to colonization order", Oikos (2008), 117:665-674.
Pitt et al. "Fungi and Food Spoilage", Third Edition, 2009, pp. 3-9 and 19-52.
Ragusa et al., "Feeding habits, post-embryonic and adult survival, mating, virility and fecundity of the predacious mite Amblyseius swirskii [Acarina: Phytoseiidae] on some coccids and mealybugs", Entomophaga (1977), 22(4):383-392.
Rakmakers et al., "Mass production and introduction of Amblyseius mckenziei and A. cucumeris", IOBC WPRS Bulletin (1983), 6(3):203-206.
Ramakers et al., "Large scale introductions of Phytoseiid predators to control thrips on cucumber", Med. Fac. Landbouww. Rijksuniv. Gent (1989), 54(3):923-929.
Ramakers et al., "Manipulation of Phytoseiid thrips predators in the absence of thrips", IOBC/WPRS Bull (1990), 13(5):169-172.
Ramakers et al., "Start of commercial production and introduction of Amblyseius mckenziei Sch. & Pr. (Acarina:Phytoseiidae) for the control of Thirps tabaci lind. (Thysanoptera: Thripidae) in glasshouses", Mededelingen Faculteit Landbouwwetenschappen Rijksuniversiteit Gent (1982), 47(2):541-545.
Rasmy et al. "A new diet for reproduction of two predaceous mites amblyseius gossipi and agistemus exsertus [acari: phytoseiidae, stigmaeidae]", Entomophaga (1987), 32(3):277-280.
Rasmy et al., "Cannibalism and interspecific predation of the phytoseiid mite, amblyseius swirskii", J Pest Sci (2004), 77:23-25.
Sampson, "The commercial development of an Amblyseius cucumeris controlled release method for the control of Frankliniella occidentalis in protected crops", The 1998 Brighton Conference—Pests and diseases (1998), 5B-4:409-416.
Schulz et al. "Identification and Biosynthesis of an Aggregation Pheromone of the Storage Mite Chortoglyphus arcuatus", ChemBioChem vol. 5, pp. 1500-1507 (2004).
Shih, "Automatic mass-rearing of Amblyseius womersleyi (Acari: Phytoseiidae)", Experimental and Applied Acarology (2001), 25(5):425-440.
Simberloff et al., "Experimental Zoogeography of Islands. A Two-Year Record of Colonization", Ecology (1970), 51(5):934-937.
Simberloff et al., "Experimental Zoogeography of Islands: The Colonization of Empty Islands", Ecology (1969), 50(2):278-296.
Sinha et al. "Feeding and Reproduction of the Grain Mite and the Mushroom Mite on Some Species of Penicillium", Journal of Economic Entomology, Dec. 1968, 61 (6) 1548-1552.
Solomon et al., "Rearing acaroid mites" Acarologia, fasc. H.S. 1964 (C.R.ler Congres Int. D'Acarologie, Fort Collins, Col., U.S.A. (1963).
Solomon et al., "Storage Fungi Antagonistic to the Flour Mite (Acarus siro L.)", Journal of Applied Ecology, vol. 1, No. 1 (May 1964), pp. 119-125.
Swirski et al., "Laboratory studies on the feeding, development and reproduction of the predaceous mites Amblyseius rubini, Swirski and Amitai and Amblyseius swirskii, Athias on various food substances", Israel Journal of Agricultural Resea (1967), 17(2):101-119.

(56) References Cited

OTHER PUBLICATIONS

Teich, "Mites of the family Phytoseiidae as predators of the tabacco whitefly, Bemisia tabaci, Gennadius", Israel Journal of Agricultural Resea (1966), 16(3):141-142.

Treat, "Mites of moths and butterflies", Cornell University Press, Ithaca and London, pp. 272-293 (1975).

Undeen et al. "The Effect of Ultraviolet Radiation on the Germination of Nosema algerae Vavra and Undeen (Microsporida: Nosematidae) Spores", J. Protozool., 37(3), 1990, pp. 194-199.

Van Houten et al. "Biological control of Western Flower Thrips in greenhouse sweet peppers using non-diapausing predatory mites", IOBC—WPRS Bulletin, Ed. J. C. van Lenteren, vol. 16, No. 2, pp. 70-80 (1993).

Van Houten et al., "Preselection of predatory mites to improve year-round biological control of western flower thrips in greenhouse crops", Entomologia Experimentalis et Applicata (1995), 74:225-234.

Van Lenteren et al., "Guidelines for quality control of commercially produced natural enemies", van Lenteren (ed.) Quality control and production of biological control agents—Theory and testing procedures. CABI Publishing, Wallingford: 265-303 (2003).

Van Rijin et al., "Pollen availability and its effect on the maintenance of polulations of Amblyseius cucumeris, a predator of thrips", Med. Fac. Landbouww. Rijksuniv. Gent. (1990), 55: 335-341.

Vanninen et al., "Amblyseius cucumeris-petopunkkien leviäminen pusseista leikkoruusukasvuston eri osiin korotettujen petien viljelyssa", Kalifornianripsiäisen (Frankiniella occidentalis) hallinta torjunta-aineiden käytön minimoivassa leikkoruusutuotannossa (2001). MTT:n julkaisuja. Sarja A 102: pp. 106-112.

Vanninen et al., "Performance of Neoseiulus cucumeris as a biocontrol agent of the Western Flower Thrips in cut roses", Bulletin of OILB/SROP (2002), 25(1):289-292.

Vitzhum, "Die Deutonympha von Carpoglyphus lactis" (Acari: Tyroglyphidae) Zool. Anz. (1940), 129: 197-201.

Wahab et al., "Mites associated with vegetable and ornamental plants in lower Egypt äcarina parasitiformes acariformes", Database Biosis Online! Biosciences information service, Philadelphia, PA, US—Database accession No. PREV197865057938, abstract, & Bulletin de la societe entomologique D'Egypte, vol. 58, 1974, pp. 359-366, ISSN: 0373.

Wharton et al. "Predatory behaviour of the mite cheyletus aversor", Animal Behaviour, vol. 20, Issue 4, Nov. 1972, pp. 719-723.

Yook et al. Effects of Ionizing Energy and Ozone Treatments on the Microbial Decontamination and Physicochemical Properties of Aloe Powders and Bee Pollen, J. Food Sci. Nutr., vol. 2, No. 2, pp. 89-95 (1997).

Zdarkova et al., "Compatibility of Cheyletus eruditus (Schrank) (Arari: Cheyletidae) and Cephalonomia tarsalis (Ashmead) (Hymenoptera: Bethylidae) in Biological Control of Stored Grain Pests", Plant Protect. Sci. (2003), 39(1):29-34.

Zdarkova et al., "Space requirements of Cheyletus eruditus (Schrank) and Cheyletus malaccensis, Oudemans (Acarina: Cheyletidae)", Advances in Stored Product Protection, Eds. Credland, P.F. et al Proceedings of the VIII IWSCPP, pp. 183-185 (2002).

Zdarkova et al., "The effects of physical factors on survival of stored food mites", Exp. Appl. Acarol. (1993), 17:197-204.

Zdarkova, "Section 4—Mites as pests of stored products. 14.1. Application of the bio-preparation 'cheyletin' in empty stores", Modern Acarology, Eds. Dusabeck & Bukva (1991), 1:607-610.

Zhang et al., "Potential of amblyseius cucumeris (Acari: phytoseiidae) as a biocontrol agent against schizotetranychus nanjingensis in Fujian, China", Systematic and Applied Acarology Special Publications (2000), 4:109-124.

Zhang, "10.4.2 Neoseiulus cucumeris" Mites of Greenhouses Part III Beneficial Mites , Oudemans, Chapter 10 Phytoseiid Mites ; pp. 186-189 (2003).

Duso et al., Availability of alternative foods can influence the impact of pesticides on predatory mites (Acari): a summary of the evidence, Zoosymposia (2011), 6:124-130.

Flechtmann et al., Studies on how Phytoseiid mites feed on spider mites and pollen, Internat. J. Acarol. (1992) 18:157-162.

Hubert et al., Combination of the antifeedant bean flour and the predator Cheyletus malaccensis suppresses storage mites under laboratory conditions, BioControl (Jun. 2009), 54(3):403-410.

McMurtry et al., Revision of the lifestyles of phytoseiid mites (Acari: Phytoseiidae) and implications for biological control strategies, Systematic and Applied Acarology (2013), 18(4):297-320.

Overmeer, Chapter 2.1.4.1.Rearing and Handling, Spider Mites: Their biology, natural Enemies and Control, World Crop Pests, vol. 1B. Elsevier Science, Amsterdam 1985, p. 161-170.

* cited by examiner

Means: 883 (live), 1325 (live+frozen); p= 0,011

Means: 375 (live), 505 (live+frozen); p= 0,002

Means: 309 (live), 480 (live+frozen); p= 0,021

Means: 116 (live), 314 (live+frozen); p= 0,000

MITE COMPOSITION COMPRISING A PREDATORY MITE AND IMMOBILIZED PREY CONTACTED WITH A FUNGUS REDUCING AGENT AND METHODS AND USES RELATED TO THE USE OF SAID COMPOSITION

The present invention in general relates to the field of biological crop protection by use of predatory mites. More particularly the present invention relates to a mite composition comprising a predatory mite and a prey. Such a mite composition is suitable for rearing the predatory mite and/or for crop protection using the predatory mite.

The use of predatory mites for biological crop protection is becoming increasingly popular in agriculture and horticulture. Currently predatory mites from the families Phytoseiidae, Laelapidae, Macrochelidae, Parasitidae, Tydeidae, Cheyletidae, Cunaxidae, Erythraeidae, Stigmaeidae are employed or have been suggested to combat pests such as phytophagous mites, thrips and whiteflies. A prerequisite for commercial use of predatory mites as biological pest control agents is their availability for an acceptable price. For this the possibility to efficiently produce them in large quantities is of importance.

During the past years methods for mass rearing have considerably improved in view of the availability of rearing preys (or alternatively referred to as rearing hosts) for predatory mites. Many of these newly available rearing preys are *Astigmatid* mites. For example reference may be made to the international applications of Koppert B. V., WO2006/057552, WO2006/071107 and WO2007/075081. In addition WO2008/015393, WO2008/104807 and EP2232986 disclose additional combinations of *Phytoseiid* predators and *Astigmatid* prey mite species. Such *Astigmatid* prey mite species have been found to be also suitable for mass-rearing of predatory species from other taxa such as predatory *Mesostigmatid* mite species, predatory *Prostigmatid* mite species.

Despite these developments in the availability of rearing preys, certain limitations in the mass rearing of predatory mites do remain and mass rearing would benefit from improvement of such limitations.

For example the living rearing preys may also be a source of stress for the predatory mites due to their motional activity, their metabolic activity, which produces metabolic gasses and metabolic heat. These effects may in particular be very considerable at high population densities. In addition live prey individuals may produce and secrete certain chemicals, such as alarm pheromones that may be disturbing for predatory mites and may even act as a defense against attacking predators. These density dependent stress factors may result in a slower population development rate and a lower maximum population density of the predatory mites due to a lower oviposition rate, a lower survival of immature and a shorter longevity of adult predatory mites. Suitable inventive solutions to eliminate or mitigate these stress factors will allow to achieve higher rearing population densities and a fast population development rate.

EP 2 380 436 discloses a mite composition comprising a population of a *Phytoseiid* predatory species and a population of an *Astigmatid* species and a method for rearing Phytoseiid predatory mites using the composition. The composition is characterized in that the population of the *Astigmatid* species is not alive. Not alive meaning that there are no live *Astigmatid* individuals at all (the prey is entirely inert).

The composition of EP 2 380 436 and its use in rearing a Phytoseiid predator may potentially reduce or eliminate disturbing stress factors induced by live prey. However, while possibly solving certain problems, this composition also has major disadvantages. The inventors of the present invention have found that dead *Astigmatid* mites are also a good fungal substrate and promote fungal growth. This problem is not recorded in the prior art. Extensive fungal growth negatively influences the population development rate and maximum population density of predatory mites.

The present invention is based on the finding that adequate fungal reduction is required when predatory mites are reared on a population of rearing preys comprising a substantial number of dead or otherwise immobilized prey individuals.

The invention therefore according to a first aspect relates to a mite composition comprising:
  a population of individuals of a predatory mite species;
  a food source for the predatory individuals comprising individuals of at least one *Astigmatid* mite species, wherein at least a fraction of the *Astigmatid* individuals is immobilized;
  optionally a food source suitable for *Astigmatid* individuals;
  and optionally a carrier for the individuals of the mite species;
  wherein immobilized *Astigmatid* individuals, and optionally the optional food source for *Astigmatid* individuals, are contacted with a fungus reducing agent.

The composition comprises individuals of a population of a predatory mite. As is known to the skilled person *Phytoseiid* predatory mites have their natural habitat on plants where they prey on pest organisms (insects and mites). They may be isolated from their natural habitats as described by de Moraes et al., 2004. Predatory mites that are particularly useful in the present invention may be selected from predatory *Mesostigmatid* mite species, predatory *Prostigmatid* mite species, in particular:
  *Mesostigmatid* mite species selected from:
    i) Phytoseiidae such as from:
      the subfamily of the Amblyseiinae, such as from the genus *Amblyseius*, e.g. *Amblyseius andersoni, Amblyseius aerialis, Amblyseius swirskii, Amblyseius herbicolus* or *Amblyseius largoensis*, from the genus *Euseius* e.g. *Euseius finlandicus, Euseius hibisci, Euseius ovalis, Euseius victoriensis, Euseius stipulatus, Euseius scutalis, Euseius tularensis, Euseius addoensis, Euseius concordis, Euseius ho* or *Euseius citri*, from the genus *Neoseiulus* e.g. *Neoseiulus barkeri, Neoseiulus californicus, Neoseiulus cucumeris, Neoseiulus longispinosus, Neoseiulus womersleyi, Neoseiulus idaeus, Neoseiulus anonymus, Neoseiulus paspalivorus, Neoseiulus reductus* or *Neoseiulus fallacis*, from the genus *Amblydromalus* e.g. *Amblydromalus limonicus* from the genus *Typhlodromalus* e.g. *Typhlodromalus aripo, Typhlodromalus laila* or *Typhlodromalus peregrinus* from the genus *Typhlodromips* e.g. *Typhlodromips montdorensis*, from the genus *Phytoseiulus*, e.g. *Phytoseiulus persimilis, Phytoseiulus macropilis, Phytoseiulus longipes, Phytoseiulus fragariae*;
      the subfamily of the Typhlodrominae, such as from the genus *Galendromus* e.g. *Galendromus occidentalis*, from the genus *Typhlodromus* e.g. *Typhlodromus pyri, Typhlodromus doreenae* or *Typhlodromus athiasae*;

ii) *Ascidae* such as from the genus *Proctolaelaps*, such as *Proctolaelaps pygmaeus* (Muller); from the genus *Blattisocius* e.g. *Blattisocius tarsalis* (Berlese), *Blattisocius keegani* (Fox); from the genus *Lasioseius* e.g. *Lasioseius fimetorum* Karg, *Lasioseius floridensis* Berlese, *Lasioseius bispinosus* Evans, *Lasioseius dentatus* Fox, *Lasioseius scapulatus* (Kenett), *Lasioseius athiasae* Nawar & Nasr; from the genus *Arctoseius* e.g. *Arctoseius semiscissus* (Berlese); from the genus *Protogamasellus* e.g. *Protogamasellus dioscorus* Manson;

iii) *Laelapidae* such as from the genus *Stratiolaelaps* e.g. *Stratiolaelaps scimitus*(Womersley) (also placed in the genus *Hypoaspis*); *Geolaelaps* e.g. *Geolaelaps aculeifer* (Canestrini) (also placed in the genus *Hypoaspis*); *Androlaelaps* e.g. *Androlaelaps casalis casalis* (Berlese);

iv) *Macrochelidae* such as from the genus *Macrocheles* e.g. *Macrocheles robustulus* (Berlese), *Macrocheles muscaedomesticae* (Scopoli), *Macrocheles matrius* (Hull);

v) *Parasitidae* such as from the genus *Pergamasus* e.g. *Pergamasusquisquiliarum* Canestrini; *Parasitus* e.g. *Parasitusfimetorum* (Berlese), *Parasitus bituberosus* Karg;

*Prostigmatid* mite species such as from:

vi) *Tydeidae* such as from the genus *Homeopronematus* e.g. *Homeopronematus anconai* (Baker); from the genus *Tydeus* e.g. *Tydeus lambi* (Baker), *Tydeus caudatus* (Dugés), *Tydeus lambi* (Baker); from the genus *Pronematus* e.g. *Pronematus ubiquitous* (McGregor);

vii) *Cheyletidae* such as from the genus *Cheyletus* e.g. *Cheyletus eruditus* (Schrank), *Cheyletus malaccensis* Oudemans;

viii) *Cunaxidae* such as from the genus *Coleoscirus* e.g. *Coleoscirus simplex* (Ewing), from the genus *Cunaxa* e.g. *Cunaxa setirostris* (Hermann);

ix) *Erythraeidae* such as from the genus *Balaustium* e.g. *Balaustium putmani* Smiley, *Balaustium medicagoense* Meyer &Ryke, *Balaustium murorum* (Hermann);

x) *Stigmaeidae* such as from the genus *Agistemus* e.g. *Agistemus exsertus* Gonzalez; such as from the genus *Zetzellia* e.g. *Zetzellia mali* (Ewing).

When selected as a *Phytoseiid* species, the mite species preferably is a *Phytoseiid* species selected from *Amblyseius swirskii*, *Amblysieus aerialis*, *Amblyseius andersoni*, *Neoseiulus barkeri*, *Neoseiulus californicus*, *Neoseiulus cucumeris*, *Neoseiulus fallacis*, *Typhlodromips montdorensis* or *Amblydromalus limonicus*.

The names of the Phytoseiid mite subfamilies, genera and species as used in relation to this invention is as referred to in de Moraes, G. J. et al., 2004, unless otherwise stated. For the species from other families see Gerson U., Smiley R. L. and Ochoa R., 2003, Mites (Acari) for pest control (Blackwell Publishing). It may be noted that alternative and equivalent names may be in use for certain mite species. For example it is known to the skilled person that *Amblydromalus limonicus* is also known by the alternative and equivalent names *Amblyseius limonicus* and *Typhlodromalus limonicus*.

The population of the predator preferably is a rearing population. In this description the term rearing must be understood to include the propagation and increase of a population by means of sexual reproduction. A rearing population may comprise sexually mature adults from both sexes, and/or individuals of both sexes of other life stages, e.g. eggs, larvae and/or nymphs, which can mature to sexually mature adults. Alternatively the rearing population may comprise one or more fertilized females. In essence a rearing population is capable of increasing the number of its individuals by means of sexual reproduction.

The mite composition further comprises a food source for the predatory individuals comprising individuals of at least one *Astigmatid* mite species. Individuals from one or more life stages of the selected *Astigmatid* mite species must be suitable prey (food source) for the individuals of the selected predator. The selection of suitable *Astigmatid* mites as a prey for selected predators is within the ambit of the knowledge of the skilled person. The *Astigmatid* mites can be isolated from their natural habitats as described by Hughes A. M., 1977, and can be maintained and cultured as described by Parkinson, C. L. (1992) and Solomon, M. E. & Cunnington, A. M. (1963)

The *Astigmatid* mite species may be selected from:

i) *Carpoglyphidae* such as from the genus *Carpoglyphus* e.g. *Carpoglyphus lactis*;

ii) *Pyroglyphidae* such as from the genus *Dermatophagoides* e.g. *Dermatophagoides pteronysinus*, *Dermatophagoides farinae*; from the genus *Euroglyphus* e.g. *Euroglyphus longior*, *Euroglyphus maynei*; from the genus *Pyroglyphus* e.g. *Pyroglyphus africanus;* iii) Glycyphagidae such as from the subfamily Ctenoglyphinae, such as from the genus *Diamesoglyphus* e.g. *Diamesoglyphus intermediusor* from the genus *Ctenoglyphus*, e.g. *Ctenoglyphusplumiger*, *Ctenoglyphus canestrinii*, *Ctenoglyphus palmifer*; the subfamily Glycyphaginae, such as from the genus *Blomia*, e.g. *Blomia freemani* or from the genus *Glycyphagus*, e.g. *Glycyphagus ornatus*, *Glycyphagus bicaudatus*, *Glycyphagus privatus*, *Glycyphagus domesticus*, or from the genus *Lepidoglyphus* e.g. *Lepidoglyphus michaeli*, *Lepidoglyphus fustifer*, *Lepidoglyphus destructor*, or from the genus *Austroglycyphagus*, e.g. *Austroglycyphagus geniculatus*; from the sub family Aëroglyphinae, such as from the genus *Aëroglyphus*, e.g. *Aëroglyphus robustus*; from the subfamily Labidophorinae, such as from the genus *Gohieria*, e.g. *Gohieria. fusca*; or from the subfamily Nycteriglyphinae such as from the genus *Coproglyphus*, e.g. *Coproglyphus stammerior* from the subfamily Chortoglyphidae, such as the genus *Chortoglyphus* e.g. *Chortoglyphus arcuatus* and more preferably is selected from the subfamily Glycyphaginae, more preferably is selected from the genus *Glycyphagus* or the genus *Lepidoglyphus* most preferably selected from *Glycyphagus domesticus* or *Lepidoglyphus destructor;* iv) Acaridae such as from the genus *Tyrophagus* e.g. *Tyrophagus putrescentiae*, *Tyrophagus tropicus*; from the genus *Acarus* e.g. *Acarus siro*, *Acarus farris*, *Acarus gracilis*; from the genus *Lardoglyphus* e.g. *Lardoglyphus konoi*, from the genus *Thyreophagus*, such as *Thyreophagus entomophagus*; from the genus *Aleuroglyphus*, e.g. *Aleuroglyphus ovatus*.

v) Suidasiidae such as from the genus *Suidasia*, such as *Suidasia nesbiti*, *Suidasia pontifica* or *Suidasia medanensis*.

A reference to the Astigmata is presented in Hughes (1977). Preferred *Astigmatid* mites may be selected from *Lepidoglyphus destructor*, Carpoglyphidae such as from the genus *Carpoglyphus* e.g. *Carpoglyphus lactis*, the genus

*Thyreophagus*, such as *Thyreophagus entomophagus*, Acaridae, *Suidasia pontifica* or *Suidasia medanensis*. Or from *Blomia* spp.

According to the present invention at least a fraction of the *Astigmatid* individuals is immobilized. Within the context of the present invention the term immobilized should be construed to mean that the *Astigmatid* individuals have been subjected to an immobilization treatment. An immobilization treatment should be construed to mean a treatment which impairs the motility that an *Astigmatid* individual has in any of its life stages. Motility being the capability of moving spontaneously and independently.

As the skilled person is aware of, life stages of *Astigmatid* mites which are motile are larvae, nymphs and adults. Thus treatments that impair the motility of any of these stages should be considered to be an immobilization treatment. In addition treatments that prevent individuals to develop from a non-motile life stage, such as from the egg stage to a motile life stage, should also be considered an immobilization treatment. According to a preferred embodiment the population of immobilized *Astigmatid* mite individuals comprise eggs, larvae, nymphs or adults, preferably all these life stages. According to a further preferred embodiment the *Astigmatid* individuals are permanently immobilized. A treatment causing death may be considered a permanently immobilizing treatment.

In the invention the *Astigmatid* individuals may be immobilized by an immobilization treatment selected from thermal treatment, such as freezing, heating, cold-shock or heat-shock treatment; chemical treatment, such as gas or fume treatment, for example gas suffocation or alcohol or ether fume treatment, preferably ethanol fume treatment; by radiation treatment, such as UV, microwave or X-ray treatment; by mechanical treatment, such as vigorous shaking, or stirring, subjecting to shear forces, collision; gas pressure treatment, such as ultrasound treatment, pressure changes, preferably pressure drops; by electrical treatment, such as electrocution; immobilising with an adhesive; or immobilisation by starvation, such as induced by water or food deprivation; immobilization by suffocation, such as by temporarily eliminating oxygen from the atmosphere or replacing oxygen by another gas. The skilled person will understand that and how these treatments may result in the immobilisation of the *Astigmatid* individuals and that the immobilisation treatment should be such that the *Astigmatid* individuals remain a suitable prey (food source) for the predatory mite individuals.

Thermal treatment may be performed by subjecting the *Astigmatid* individuals during a sufficiently long time to a temperature outside the ambient range, such that immobilization is induced. The temperature outside the ambient range may for example be selected from $\leq 3°$ C., $\leq 2°$ C., $\leq 1°$ C., $\leq 0°$ C., $\leq -1°$ C., $\leq -2°$ C., $\leq -3°$ C., $\leq -4°$ C., $\leq -5°$ C., $\leq -6°$ C., $\leq -7°$ C., $\leq -8°$ C., $\leq -9°$ C., $\leq -10°$ C., $\leq -18°$ C., $\leq -20°$ C. There is no lower limit for the temperature outside the ambient range other than the practical limits and the temperature outside the ambient range may be as low as $-78°$ C., $-79°$ C., $-80°$ C., $-194°$ C., $-195°$ C., $-196°$ C., $-197°$ C. Alternatively the temperature outside the ambient range may be selected from $\geq 40°$ C., $\geq 41°$ C., $\geq 42°$ C., $\geq 43°$ C., $\geq 44°$ C., $\geq 45°$ C., $\geq 46°$ C., $\geq 47°$ C., $\geq 48°$ C., $\geq 49°$ C., $\geq 50°$ C. The temperature outside the ambient range may be as high as $55°$ C., $60°$ C. or $65°$ C., $70°$ C., $75°$ C., $80°$ C.

Chemical treatment may be performed by subjecting the *Astigmatid* individuals during a sufficiently long time to an immobilizing chemical such that immobilization is induced. The immobilizing chemical may be in the form of a gas or a fume, e.g. a gas that causes suffocation by expelling oxygen and/or by being toxic such as $CO_2$, $N_2$, CO, NO, $NO_2$. Alternatively the immobilizing chemical may be a different chemical known to potentially interfere with animal physiology for example alcohols such as ethanol or methanol or combinations or ethers such as diethylether. Preferably the immobilizing chemical does not leave toxic traces, as the immobilized *Astigmatid* individuals serve as a food source for the predatory mites.

Radiation treatment may be performed by subjecting the *Astigmatid* individuals during a sufficiently long time to immobilizing radiation such that immobilization is induced. The immobilizing radiation may be selected from UV, X-ray or microwave radiation.

Immobilisation by mechanical means may be performed by any mechanical means dissipating sufficient energy to cause an immobilizing effect. This may be achieved by vigorous shaking, or stirring, especially in the presence of particles that may collide with the mites to be immobilized. Collision may also be effected by acceleration of the mites by means of a gas stream and collision against a number of objects at least partially blocking the gas flow, or by bringing the mites in a turbulent gas flow, preferably together with additional particles carried by the turbulent gas flow (such as a turbulent airflow) and allowing the mites to collide with these particles. Alternatively ultra sound treatment may also be used.

According to a different embodiment *Astigmatid* mites may be immobilised with an adhesive. For example by making them stick to a surface, or alternatively by making their limbs stick, thus imparing their motility.

Starvation may be a further means to achieve immobilization. Starvation may be effected by water or food deprivation. Water and food deprivation should be considered the circumstance where the amount of water or food made available is less than the amount required for normal metabolism under the existing conditions in the mite's environment.

The immobilization treatment should be sufficiently effective to immobilize at least a fraction of the individuals of the *Astigmatid* mite. At least a fraction should be understood to mean a fraction or substantially all. The fraction of immobilized *Astigmatid* individuals may be $\geq 10\%$, $\geq 20\%$, $\geq 30\%$, $\geq 40\%$, $\geq 50\%$, $\geq 60\%$, $\geq 70\%$, $\geq 80\%$, $\geq 90\%$, $\geq 95\%$, or $\geq 97\%$. Preferably the fraction immobilized *Astigmatid* individuals is 50-90%, more preferably 70-90%. The fraction immobilized *Astigmatid* individuals comprises one or more life stages of the *Astigmatid* mite selected from eggs, larvae, nymphs or adults.

Thus according to the invention it is not necessary that the population of the *Astigmatid* individuals is completely dead or inert (as there may be a non-immobilized motile fraction) for obtaining positive effects in respect of a reduction of stress presented to the predators by the *Astigmatid* individuals. In addition the presence of a small population of motile *Astigmatid* individuals may present additional benefits by their mycophagous behavior, production of antifungal exudates and/or provision of a fresh (live) food source as discussed below. Also immobilized *Astigmatid* individuals need not be metabolically inactive. Certain immobilization treatments may still allow metabolic activity while impairing motility. Metabolically active immobilized *Astigmatid* individuals may also be considered such a source of fresh food for the predators.

According to the invention the immobilized *Astigmatid* individuals and any non-immobilized individuals, when present, may be from the same species. However, according to certain embodiments the immobilized Astigmatid individuals and any non-immobilzed individuals, when present, may alternatively be from differing species. This creates variabilitity in the selection of the *Astigmatid* species present in the composition. Individuals from certain species could be preferred for use as an immobilized food source, while individuals from other species may be preferred for functions performed by live individuals, such as fungal reduction.

In the composition according to the invention the ratio of predatory individuals relative to *Astigmatid* individuals may be from about 100:1 to 1:100, such as about 1:1 to 1:50, e.g. about 1:4, 1:10, 1:20 or 1:30. The composition according to the invention thus may contain lower ratio's of predatory individuals relative to *Astigmatid* individuals. Thus more prey is available for the predators. This is beneficial when rearing predatory mites.

As discussed above with the composition of the present invention higher predator densities may be sustained in a medium comprising a carrier. Thus according to a preferred embodiment the composition comprises a carrier and contains ≥10, ≥50, ≥100, ≥150, ≥200, 250, ≥300, ≥350, ≥400, up to 450 predatory individuals, preferably Phytoseiid individuals, per ml carrier.

For fungal reduction immobilized *Astigmatid* individuals are contacted with a fungus reducing agent. In contacting immobilized *Astigmatid* individuals with the fungus reducing agent, the fungus reducing agent is allowed to have access to immobilized *Astigmatid* individuals, preferably substantially all immobilized *Astigmatid* individuals, such that it can exert its antifungal action. The contacting with the fungus reducing agent therefore is such that a fungus reducing effect is obtained. As the skilled person will understand this fungus reducing effect should be sufficient to allow rearing of the predator in the composition. Due to contacting with the immobilized *Astigmatid* individuals with the fungus reducing agent, any material associated with the, immobilized *Astigmatid* individuals, such as food source for these *Astigmatid* individuals, may also be contacted with the fungus reducing agent and thus may also be effectively subjected to a fungus reducing treatment.

A fungus reducing agent is any agent reducing fungal growth for example by slowing or preventing fungal growth such as by interfering with fungal metabolism or reducing fungal growth by destruction of fungal biomass. The fungus reducing agent may comprise chemical fungus reducing agents such as a natural or synthetic fungicide, for example a natural fungicide selected from citral, neral, 2,3-epoxyneral, geranial, farnesal, α-acaradial, β-acaradial, or natamycin (pimaricin).

Alternatively the fungus reducing agent may comprise a biological fungus reducing agent such as a population of fungivorous mite individuals. Fungivorous (or mycophagous) mites are mites that feed on fungal biomass and thus may reduce and control fungal growth. Preferably the fungivorous mite individuals are from an *Astigmatid* species, such as a species selected from the Acaridae, such as *Tyrophagus putrescentiae, Thyreophagus entomophagus, Acarus farris, Acarus siro, Aleuroglyphus ovatus*; Glycyphagidae, such as *Lepidoglyphus destructor, Glycyphagus domesticus*; Carpoglyphidae, such as *Carpoglyphus lactis*; Suiidasidae, such as *Suiidasia pontifica, Suidasia medanensis, Suiidasia nesbiti*; Pyroglyphidae, such as *Dermatophagoides farinae, Dermatophagoides pteronyssinus*. The skilled person will understand that in order to perform their mycophagous function the fungivorous mite individuals must be alive and preferably must be motile. Motile fungivorous individuals may form at least a part of the non-immobilized fraction of the *Astigmatid* individuals.

A biological fungus reducing agent may also be selected as a population of a mite species producing antifungal exudates such as citral, neral, geranial, farnesal, α-acaradial or β-acaradial. Such mite species producing antifungal exudates may be selected from the order Astigmata preferably from *Lepidoglyphus destructor, Acarus siro, Lardoglyphus konoi, Caloglyphus polyphyllae; Tyrophagus putresecntiae, Tyrophagus neiswanderi, Tyrophagus pernisciosus; Rhizoglyphus robini*; from the genus *Carpoglyphidae*, such as *Carpoglyphus lactis*; from the Suiidasidae, such as *Suiidasia Pontifica, Suidasia medanensis, Suiidasia nesbiti*. For the antifungal exudates producing mite individuals it is not necessary that they are motile. Certain immobilization treatments, such as immobilization by using an adhesive or certain mechanical immobilisation techniques, may still allow metabolic activity of the antifungal exudates producing mite individuals, thus also allowing production of antifungal exudates. It is however preferred that, when used, the antifungal exudates producing mite individuals are motile. In this way antifungal exudates may be more effectively distributed in the composition. Motile antifungal exudates producing mite individuals may from at least a part of the non-immobilized fraction of the *Astigmatid* individuals.

The selection of a *fungivorous* mite species and antifungal exudates producing mite species from the *Astigmata* is preferred in view of the fact that this order harbours many species having the desired mycophagous behaviour or antifungal exudates producing activities. In addition species from this order can also serve as prey for the predatory mite individuals. Motile (non-immobilized) *Astigmatid* individuals may provide an additional food source for the predatory individuals. This will present a source of fresh food to the predators. This may be important for providing labile nutrients, such as vitamins, that cannot be sufficiently preserved in immobilized prey mites, to the predators. This may add to the health status of the predatory mites. This health status may be a factor contributing to the versatility and/or agility of the predators in respect of their predatory behaviour.

According to an embodiment of the invention the composition comprises a food substance suitable for *Astigmatid* individuals. Selection of suitable food substances is within the ambit of the knowledge of the skilled person and is for example disclosed in WO2006/057552, WO2006/071107, WO2007/075081, WO2008/015393, WO2008/104807 and EP2232986. The presence of a suitable food substance is beneficial in case the composition comprises live *Astigmatid* individuals. But also in case the composition comprises only dead *Astigmatid* individuals, the food substance may be present in the composition due to transfer of the food source from the rearing medium of the *Astigmatid* mites.

This is a major difference with the composition of EP 2 380 436 discussed above. Any remainders of the food source for the *Astigmatid* mites are a potential substrate for fungi and will promote fungal growth. Therefore EP 2 380 436 requires removal of the food source. EP 2 380 436 suggests to remove the food source by exhaustion. However, this is impractical and would mean that rearing of the *Astigmatid* mite must be controlled on the basis of the food source status instead of the population development of the *Astigmatid* mite. In the rearing practice this is undesirable. In addition a continuous process would not be possible and rearing must be performed discontinuously. Removal of the food source by any other means would be laborious and is prone to the loss of *Astigmatid* biomass, introducing a source of inefficiency. In the composition according to the present invention removal of the food source is not necessary in view of the fact that according to certain embodiments for fungal reduction the food source may be contacted with a fungus reducing agent. The contacting with the fungus reducing agent is such that a fungus reducing effect is obtained. As the skilled person will understand this fungus reducing effect should be sufficient to allow rearing of the predator in the composition.

In a preferred embodiment the composition comprises a carrier for the individuals of the mite species. The carrier can be any solid material which is suitable to provide a carrier surface to the individuals. Preferably the carrier provides a porous medium, which allows exchanges of metabolic gases and metabolic heat produced by the mite populations and by metabolic activity of the carrier, food source for the *Astigmatid* prey mites and by microorganisms growing on the medium. Examples of suitable carriers are plant materials such as (wheat) bran, saw dust, corn cob grits, vermiculite, etcetera. If a food substance suitable for the *Astigmatid* individuals is included in the composition, the carrier itself may comprise a suitable food substance. The use of a carrier comprising finely divided carrier elements is popular in view of the possibility to maintain the mite culture as a three-dimensional culture.

According to a preferred embodiment the carrier for the individuals of the mite species comprises carrier elements, preferably carrier elements having a longest axis of about 1.0-15.0 mm, such as 3.0-9.0 mm and wherein the stacking of the carrier elements comprises shelters suitable for predatory mite individuals. In general terms a shelter may be defined as a dwelling place providing refuge from external influences. The shelters of the carrier according to the invention provide that to the mite individuals. On the basis of the disclosure of the present invention, in combination with his common general knowledge, the skilled person will be able to understand the structural requirements for a mite shelter. Thus the skilled person will be able to design and/or select suitable carriers comprising mite shelters, in particular shelters suitable for commercially relevant mites selected from predatory mites or rearing preys.

According to an embodiment of the invention sheltering may be provided in an area where the material of the carrier element shields a mite individual, when located in this area, from its surroundings in at least 3 directions having orthogonal or reversed relations. Shielding from the surroundings should be understood as, to at least reduce, preferably to restrict and most preferably to substantially eliminate, disturbing external interactions. Such disturbing external interactions in particular are produced or brought about by other mites in the composition, such as for example movement and associated body contact with other mites. But may for example also be cannibalistic predation by individuals from the same species, in case the mite is a predatory mite. It should be understood that all predatory mites to some extend display cannibalistic behaviour. Such disturbing interactions negatively influence the population development rate because they negatively influences one or more of the oviposition rate, survival and longevity of the mite individuals. The intensity of these disturbing interactions between conspecific predatory mite individuals will typically increase at higher population densities. However, the commercial producer of mites aims to achieve as high population densities and as high population development rates as possible in order to reduce the production cost as much as possible. According to an embodiment of the invention sheltering may be provided by shielding the mite individuals from the disturbing interactions. This shielding may be provided by reducing the access to the mite individuals.

As will be understood, directions having orthogonal or reversed relations correspond to directions along the 6 axes (positive X, negative X, positive Y, negative Y, positive Z, negative Z) of an imaginary orthogonal (or Cartesian) three dimensional coordinate system in the direction out of the origin (0,0,0), where the mite individual is in the origin. These directions are either perpendicular (orthogonal) or reversed in direction. In three-dimensional space the maximal number of these directions is 6, as is depicted in FIG. 1.

According to an embodiment of the invention the mite individual, when located in a sheltering area, is shielded from its surroundings in at least 3 such directions, preferably in at least 4 of such directions, most preferably in at least 5 of such directions, such as in 5 such directions. Shielding in 3 such directions may be provided by a structure similar to a corner formed between 3 planes such as presented in FIG. 2 or the structure presented in FIG. 3. Shielding in at least 4 of such directions may be provided by a structure such as a "box" open at 2 sides as presented in FIG. 4. Shielding in 5 directions would be provided in the situation of FIG. 3, where a $5^{th}$ horizontal plane is placed on the side wall of the 4 plane "box", such that an open cube is obtained.

In order to shield the mite individuals from external influences brought about by other mites in the composition it is preferred that the shelters are dimensioned such that the volume of the shelter is from 1-140 $mm^3$, such as 2-120 $mm^3$, 2-100 $mm^3$, 2-80 $mm^3$, 2-70 $mm^3$, 2-60 $mm^3$, 2-50 $mm^3$, 2-40 $mm^3$, 2-30 $mm^3$, 2-25 $mm^3$, 2-20 $mm^3$, 2-18 $mm^3$, 2-16 $mm^3$, 2-14 $mm^3$, 2-12 $mm^3$, 2-10 $mm^3$, 2-8 $mm^3$, 2-6 $mm^3$, or 2-4 $mm^3$. This reduces the possibility that too many mite individuals are present in a shelter, which may give a disturbing effect.

It is evident that the shelters must be accessible by the mite individuals. In this respect it should be noted that areas not accessible for the mites cannot be qualified as shelters. According to certain embodiments of the invention in order to have good accessibility for mite individuals an area may have an access having an access diameter of at least 0.3-1.2 mm, such as 0.5-1.0 mm or 0.5-0.8 mm and an access area of at least 0.25-1.44 $mm^2$, 0.30-1.20 $mm^2$, 0.30-1.00 $mm^2$, 0.30-0.80 $mm^2$, 0.30-0.90 $mm^2$.

Mite shelters may be provided by voids, such as voids formed by coves, recesses, pores, chambers, cavities, niches, pits, pockets, tubes, domes, tubs and alike structures. Such voids preferably conforming to the dimensions presented above for the volume and/or access are suitable as mite shelters.

Shelters for the mite individuals may be present on or in individual carrier elements present in the stacking. That is to say individual carrier elements in the stacking comprise structures suitable as mite shelters. Alternatively the mite shelters may be formed between carrier elements in the stacking. That is to say in the stacking of carrier elements a plurality of carrier elements together form structures suitable as mite shelters. A "carrier element stacking" is to be understood to mean a three dimensional ordering of a multitude of carrier elements. The term "ordering" includes a random ordering.

Within the present invention carrier elements derived from chaff may be used. The skilled person will know the meaning of the term chaff and will understand that chaff is the dry, scaly protective casings (husks) of the seeds of grass species (in particular cereal grains), or similar fine, dry, scaly plant material such as scaly parts of flowers, or finely chopped straw. According to a preferably embodiment the chaff is derived from a grass (*Poaceae* or alternatively *Gramineae*) species, most preferably chaff from a cereal species, such as chaff from wheat, *oryza* species, rye, oats or millet. Husks are particularly preferred. Especially husks from millet have excellent external and internal dimensions which make them highly suitable as a mite rearing substrate providing suitable shelters.

Species comprised within the term millet for the present invention include: Pearl millet or Bajra (*Pennisetum glaucum*); Foxtail millet (*Setaria italica*); Proso millet, common millet, broom corn millet, hog millet or white millet (*Panicum miliaceum*); Finger millet (*Eleusine coracana*) (Also known as Ragi, Nachani or Mandwa in India), Indian barnyard millet or Sawa millet (*Echinochloa frumentacea*); Japanese barnyard millet (*Echinochloa esculenta*); Kodo millet (*Paspalum scrobiculatum*); Little millet (*Panicum sumatrense*); Guinea millet (*Brachiaria deflexa=Urochloa deflexa*); Browntop millet (*Urochloa ramosa=Brachiaria ramosa=Panicum ramosum*). Teff (*Eragrostis tef*) and fonio (*Digitaria exilis*) are also often called millets, as more rarely are sorghum (*Sorghum* spp.) and Job's Tears (*Coix lacrimajobi*). For the present invention these species are also within the term millet.

Apart from the dimensions of the carrier elements and their structural configuration suitable to provide mite shelters, it is preferred that the carrier elements are inert in terms of biodegradation. This means that the carrier material is a poor growing substrate for microorganisms such as fungi and/or bacteria. This aids in controlling microbial growth, such as fungal growth, which is a potential problem under mite rearing conditions. Chaff and in particular the preferred chaff varieties discussed above are poor growing substrates for microorganisms, especially for fungi.

According to a further aspect, the present invention relates to a method for rearing a predatory mite comprising:
  (i) providing a composition according to the invention
  (ii) allowing the predatory individuals to feed on individuals of the *Astigmatid* population.

Methods for rearing of predatory mites wherein a population of the predator is brought in association with a population of an *Astigmatid* mite and wherein individuals of the predator are allowed to feed on individuals of the *Astigmatid* population are known in the art. The method according to the present invention is distinguished over the prior art methods in that in the composition according to the invention at least a fraction of the *Astigmatid* individuals is immobilized and immobilized *Astigmatid* individuals are contacted with a fungus reducing agent.

The technical aspects of the composition according to the invention have already been discussed above.

A further aspect of the invention relates to the use of a composition comprising a population of individuals from at least one *Astigmatid* mite species, wherein at least a fraction of the *Astigmatid* individuals is immobilized, and immobilized *Astigmatid* individuals are contacted with a fungus reducing agent, for rearing a predatory mite. As will be evident from the description above and the experiments below, the use of a population of an *Astigmatid* mite species, wherein a fraction of the *Astigmatid* individuals is immobilized, has certain benefits for rearing a predatory mite.

Yet a further aspect of the invention relates to a rearing system for rearing a predatory mite, said system comprising a container holding the composition according to the invention. According to a preferred embodiment the container preferably comprises an exit for at least one motile life stage of the predatory mite, more preferably an exit suitable for providing a sustained release of said at least one motile life stage.

According to another aspect the invention relates to the use of the composition of the invention or the rearing system according to the invention for controlling a crop pest.

The pest may be selected from, white flies, such as *Trialeurodes vaporariorum* or *Bemisia tabaci*; thrips, such as *Thrips tabaci* or *Frankliniella* spp., such as *Frankliniella occidentalis*, spider mites such as *Tetranychus urticae*, or other phytophagous mites such as *Polyphagotarsonemus*.

The crop may be selected from, but is not restricted to (greenhouse) vegetable crops such as tomatoes (*Lycopersicon esculentum*), peppers (*Capsicum annuum*), eggplants (*Solanum melogena*), Curcubits (Cucurbitaceae) such as cucumbers (*cucumis sativa*), melons (*cucumis melo*) watermelons (*Citrullus lanatus*); beans (*Phaseolus vulgaris*); soft fruit (such as strawberries (*Fragaria x annanassa*), raspberries (*Rubus ideaus*)); (greenhouse) ornamental crops (such as roses, gerberas, chrysanthemums) or tree crops such as *Citrus* spp.

A further aspect of the invention relates to a method for biological pest control in a crop. The method comprises providing the composition of the invention to said crop. The pest and the crop may be selected as described above.

In the method according to the invention the composition may be provided by applying an amount of said composition in the vicinity, such as on or at the basis of a number of crop plants. The composition may be provided to the crop plant simply by spreading it on the crop plant or at the basis of the crop plant as is common practice for employing predatory mite compositions for augmentative biological pest control. The amount of the composition which may be provided to each individual crop plant by way of spreading may range from 1-20 ml such as 1-10 ml, preferably 2-5 ml. Alternatively the composition may be provided to the number of crop plants in the rearing system according to the invention which is suitable for releasing the predatory mite in a crop. The rearing system may be placed in the vicinity, such as in or at the basis, of a number of crop. In the method for biological pest control according to the invention it may not be necessary to provide the composition to all crop plants. As commercial crops are normally densely cultivated. The predatory mites may spread from one crop plant to another. The number of crop plants which must be provided with the composition according to the invention in order to provide sufficient crop protection may depend on the specific circumstances and can be easily determined by the skilled person based on his experience in the field. Usually the number of predatory mites released per hectare is more determining. This number may range from 1000-3 million per hectare, typically 250.000-1 million or 250.000-500.000.

The invention will now be further illustrated with reference to the attached figures and examples. It should be emphasized that these figures and examples are only illustrative and by no means restrict the scope of the invention as defined in the claims.

FIG. 1 presents an three dimensional orthogonal (Cartesian) coordinate system. Along the axes X, Y, Z six directions out of the origin (0,0,0) may be defined (along positive X, along negative X, along positive Y, along negative Y, along positive Z, along negative Z). These directions are either perpendicular (orthogonal) or reversed in direction.

Figure 2:
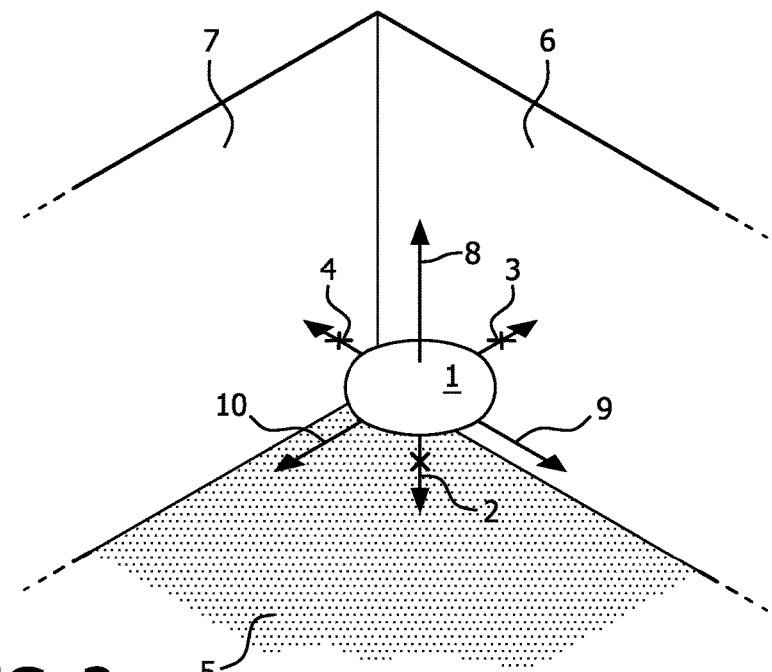

FIG. 2 presents a schematic overview of a shelter wherein a mite individual (1) is shielded from interaction with its surrounding in three directions indicated by arrows (2), (3), (4). The sheltering is provided by a floor plane (5), a first side plane (6) and a second side plane (7). Interacting influences may still come from the surroundings from directions indicated by arrows (8), (9), (1).

Figure 3:
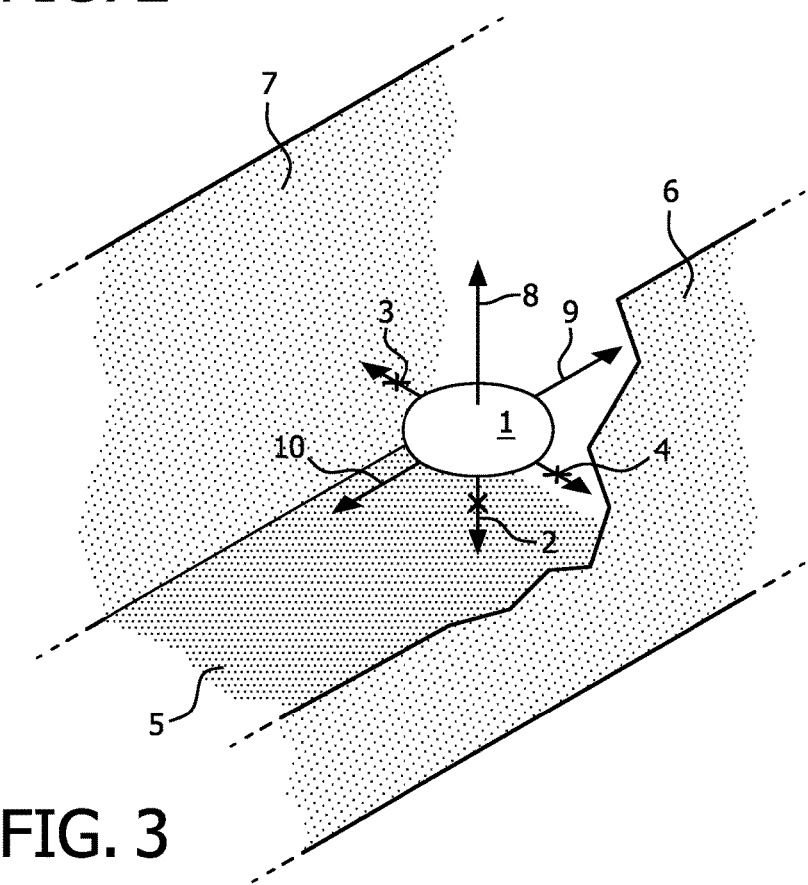

FIG. 3 presents a schematic overview of an alternative shelter wherein a mite individual (1) is shielded from interaction with its surrounding in three directions indicated by arrows (2), (3), (4). The sheltering is provided by a floor plane (5), a first side plane (6) and a second side plane (7). Interacting influences may still come from the surroundings from directions indicated by arrows (8), (9), (10).

Figure 4:
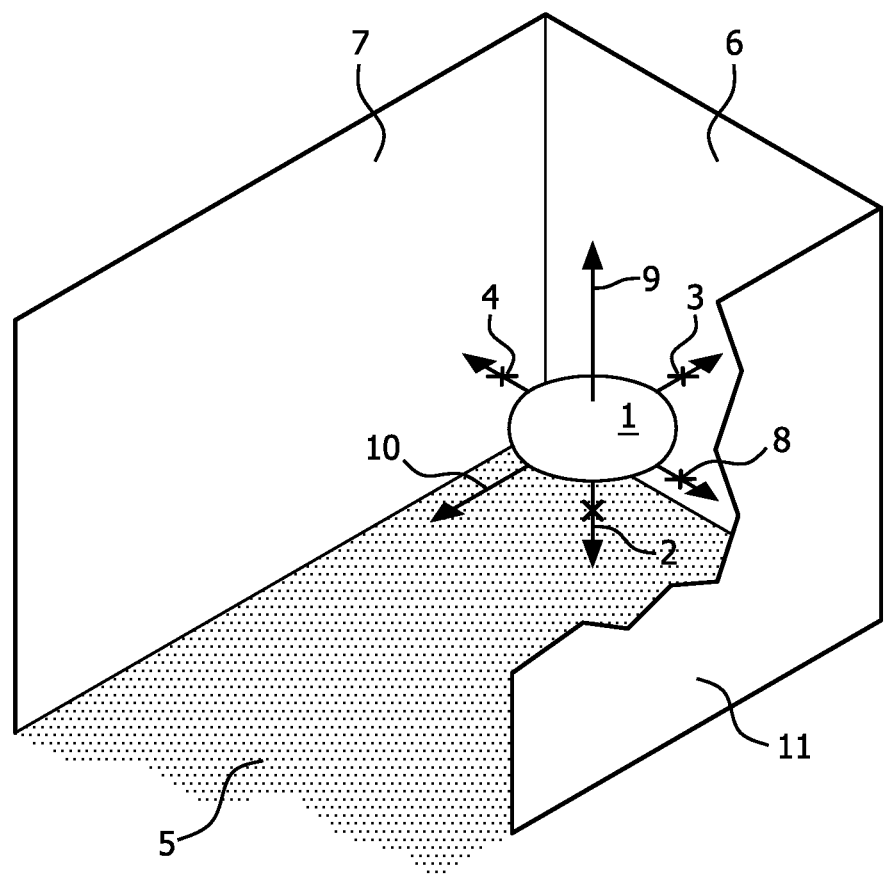

FIG. 4 presents a schematic overview of a shelter wherein a mite individual (1) is shielded from interaction with its surrounding in four directions indicated by arrows (2), (3), (4), (8). The sheltering is provided by a floor plane (5), a first side plane (6), a second side plane (7) and a third side plane (11). Interacting influences may still come from the surroundings from directions indicated by arrows (9), (10). It will be clear that the mite individual may be further shielded from interactions from the surroundings if a covering plane is located on the side planes (6), (7), (11). In addition, shielding from the surroundings may be further enhanced if a further side plane would be placed perpendicular to side plane (7). In this way the mite individual (1) would also be shielded from the surrounding in the direction indicated by arrow (10).

It should be understood that while all schematic representations of FIGS. 1-4 are presented in rectangular geometry, similar shielding effects may be provided by non rectangular structures such as coves, recesses, pores, chambers, cavities, niches, pits, pockets, tubes, domes, tubs and alike structures.

Figure 5:
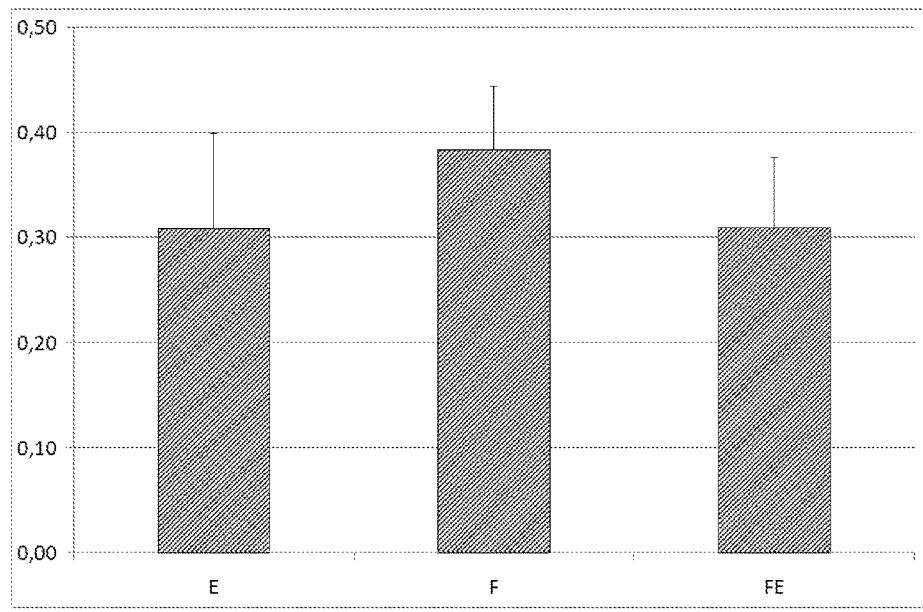

FIG. 5 provides a graphical presentation of the results from example 3 as the average fraction of mites retrieved from the differently treated foods.

Figure 6:
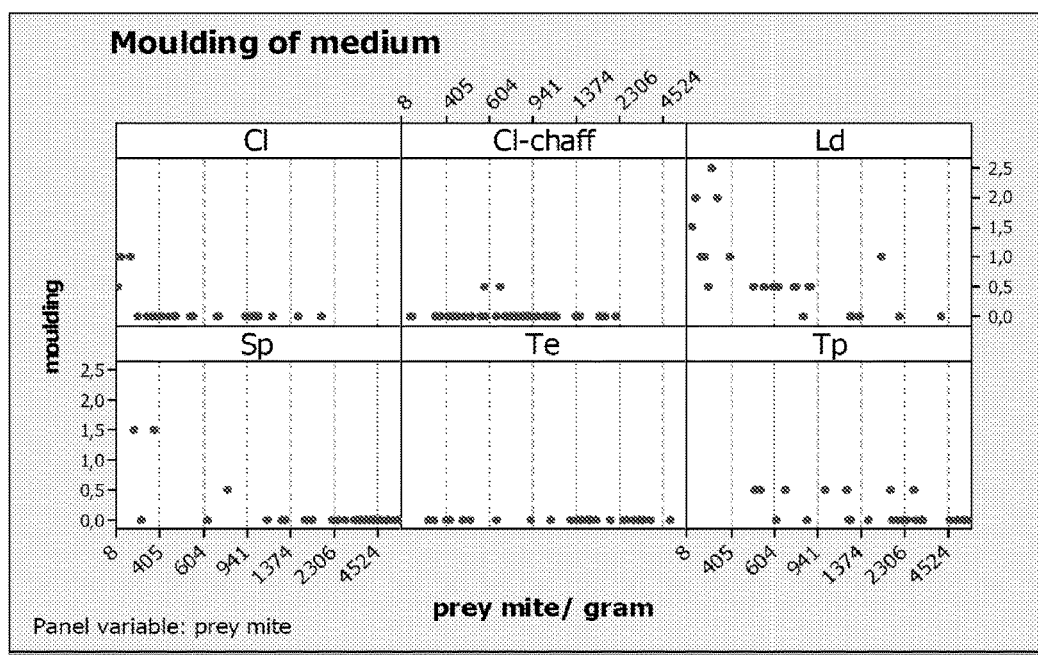
Figure 7A:
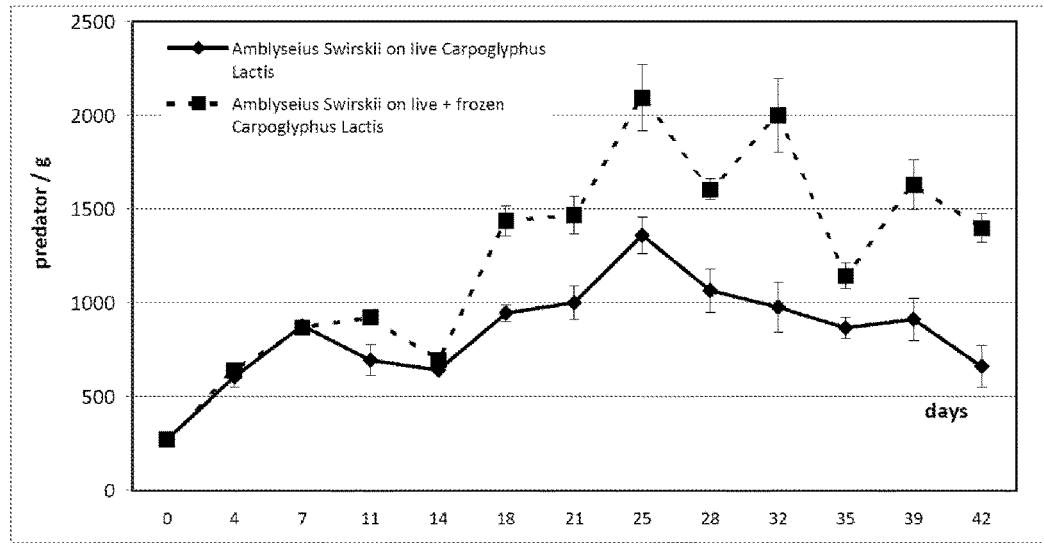
Figure 7B:
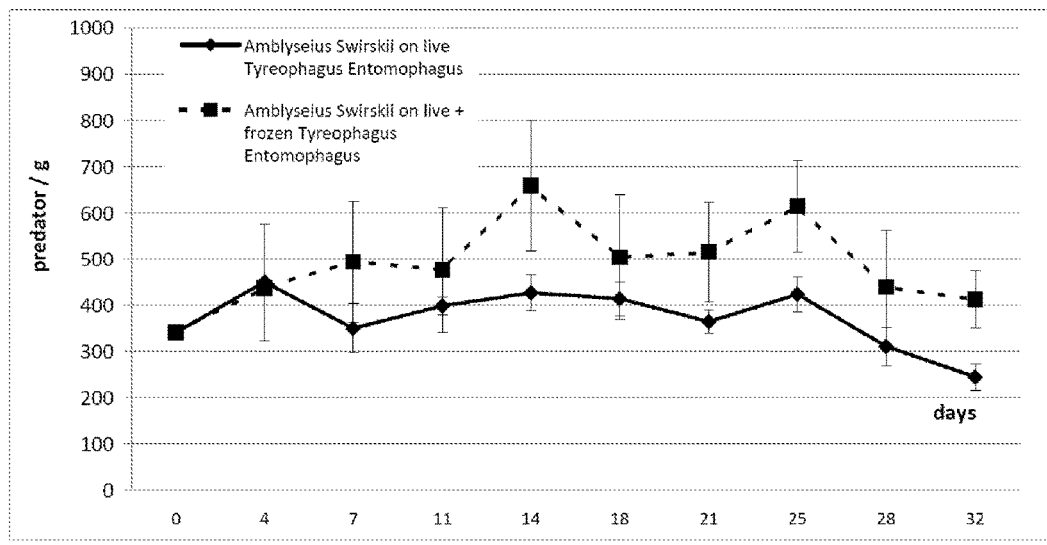
Figure 7C:
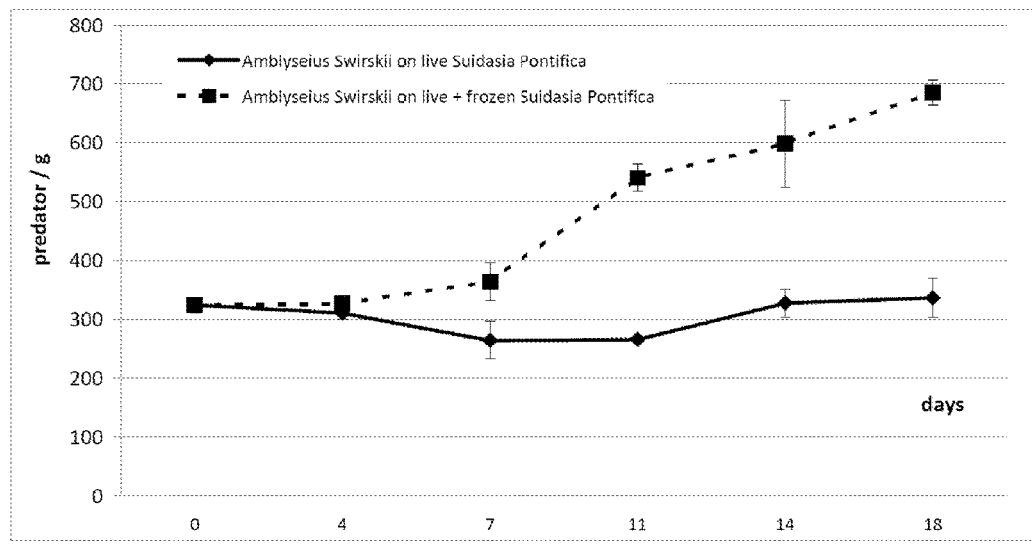
Figure 7D:
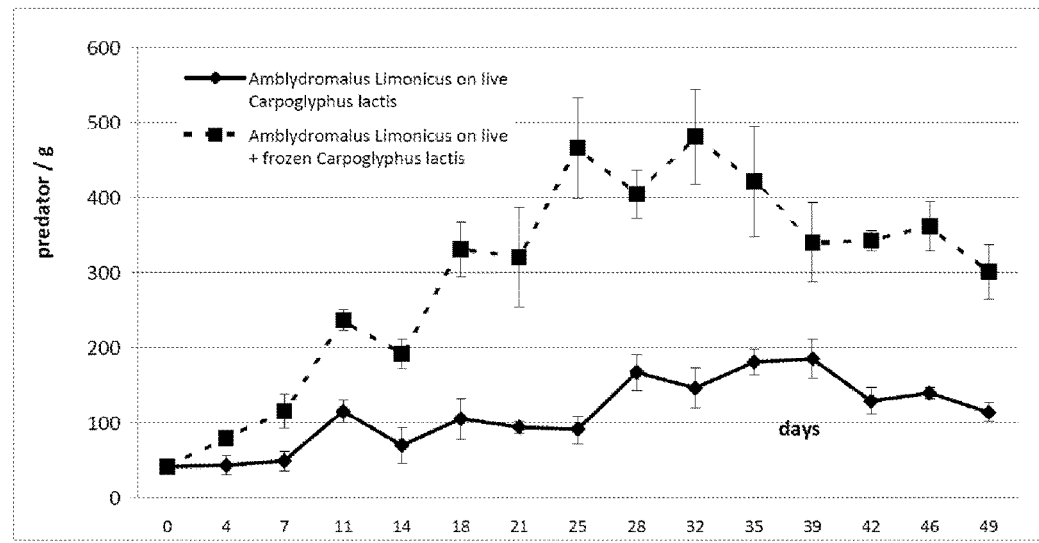

FIG. 6 presents results from example 5 as dot plots of moulding scores on bran and millet chaff carrier in relation to prey mite densities.

FIGS. 7a to 7d graphically present results of different rearings of *Amblyseius swirskii* and *Amblydromalus limonicus* performed in example 6.

Figure 8A:
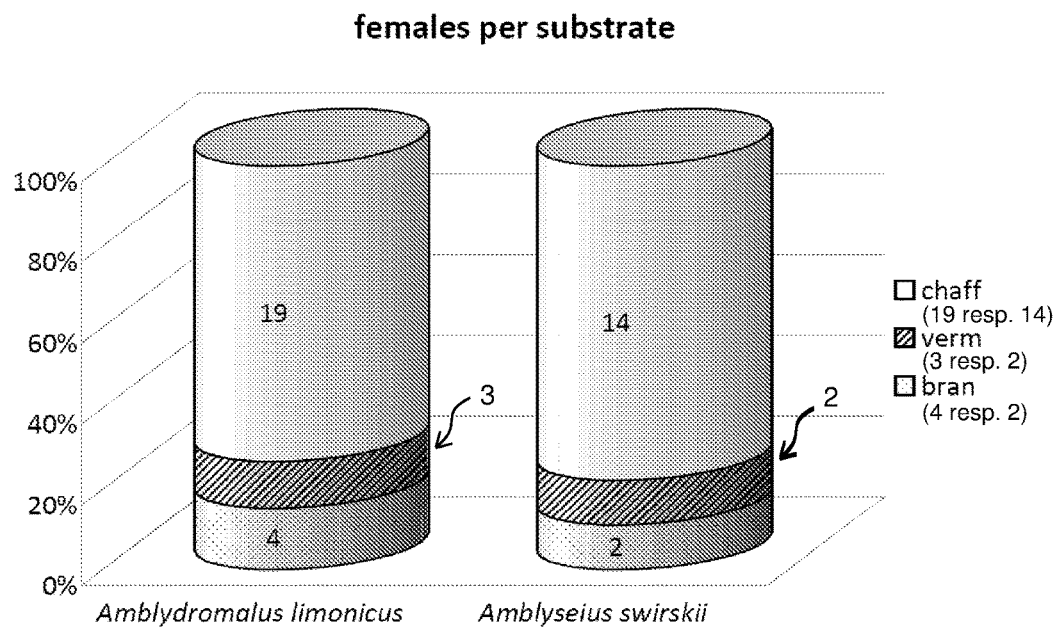
Figure 8B:
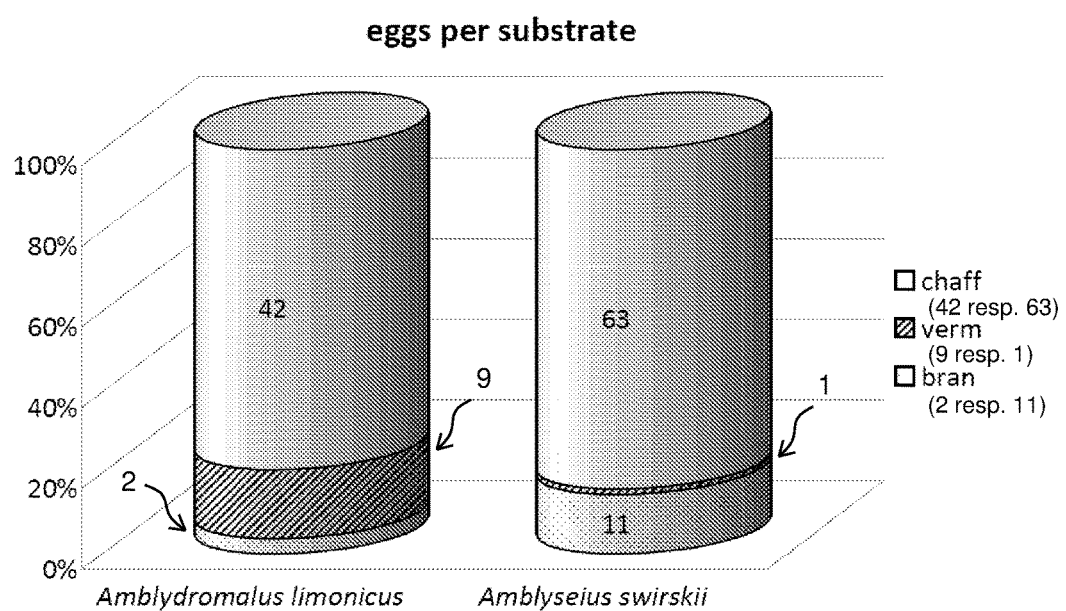

FIGS. 8a and 8b show total number of females found in carrier substrates tested in example 7.

Figure 9:
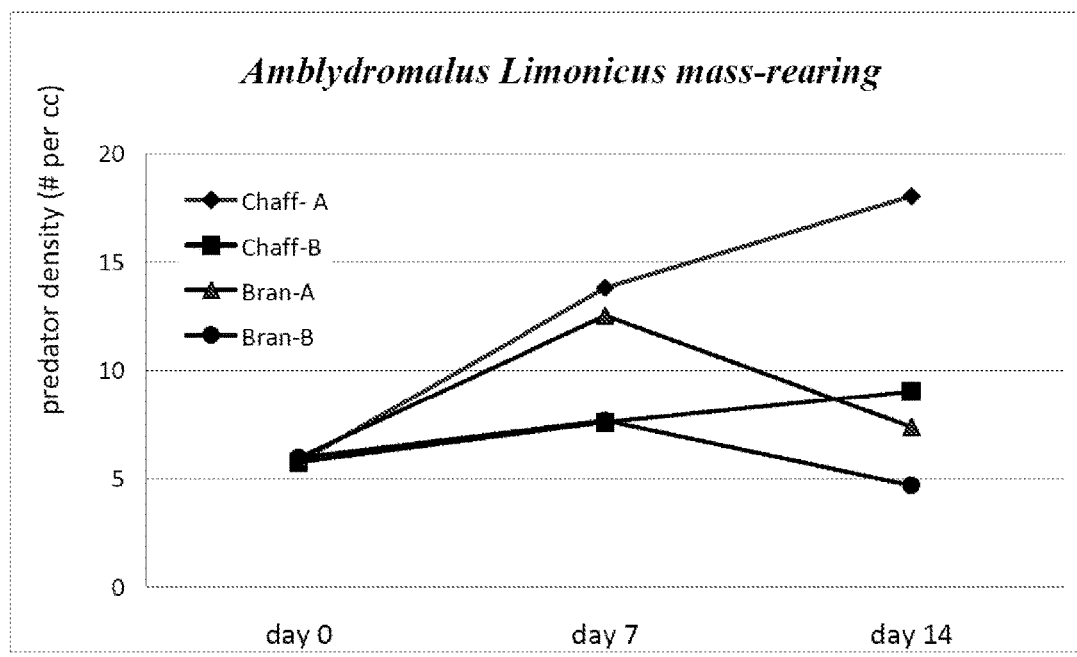

FIG. 9 graphically presents results of rearings of *Amblydromalus limonicus* performed in example 8.

EXAMPLE 1

Setup

A moulding test was performed on 6 test samples (A), (B), (C), (A+), (B+), (C+). These mixtures were prepared from the following ingredients (1) a population of pure *Carpoglyphus lactis* consisting of all motile life stages. This sample was not associated with food particles and had a moisture content of 70% (±1%). (2) The mites from (1) frozen at −20° C. in a closed container during 24 hours and defrosted prior to use. (3) consisted of *Carpoglyphus lactis* in its rearing medium (containing bran and food particles), frozen for 4 days at −20° C. in a closed container. (4) moist vermicullite (particle sizes<2 mm, moisture content 15.8%). Using these ingredients, several mixes were prepared in duplo in small cups. In a same set of cups, 0.1 g (±0.01 g) of live *Carpoglyphus lactis* (pure) mites were added to all of the mixes. The severity of moulding (mycelium growth and sporulation) was observed on day 2, 4 and 6 at two humidities (93% and 85%) and 25° C.

Results

The results are presented in table 1.1 below.

TABLE 1.1

| Startup Mix | Carrier (4) | food | extra | RH 85% day 4 | RH 85% day 6 | RH 93% day 4 | RH 93% day 6 |
|---|---|---|---|---|---|---|---|
| A | — | 1 g pure (2) | — | ++ | ++ | ++ | +++ |
| B | — | 3 g medium (3) | — | + | +++ | +++ | +++ |
| C | 5 g | 1 g pure (2) | — | + | ++ | + | ++ |
| D | 3 g | 3 g medium (3) | — | ++ | +++ | ++ | +++ |
| A+ | — | 1 g pure (2) | live Cl (1) | − | − | + | ++ |
| B+ | — | 3 g medium (3) | live Cl (1) | − | − | + | − |
| C+ | 5 g | 1 g pure (2) | live Cl (1) | + | + | − | ++ |
| D+ | 3 g | 3 g medium (2) | live Cl (1) | − | − | − | − |

− means no moulding,
+ a litte,
++ mediocre and
+++ maximum amount of moulding (food totally covered by fungi and not accessible).

The results show that moulding of organic matter was clearly visible in all cups not containing live *C. lactis* mites from day 4 onwards. It was clearly observed that frozen prey mites in pure form were susceptible to moulding. When prey mite rearing medium was included, susceptibility to moulding increased. Live mites disappeared when no food matter was available (A+ and C+) and hence moulding had a chance.

The type of moulding was different in morphology. When organic matter was in close contact (no carrier or small clumps), mycelium formed a complete network and caused the mixture to clump. When food particles were isolated by the carrier, sporulation was more observed.

Moulding of all food types was observed in all mixtures and humidities appropriate for predatory mite rearing. Lowering the fraction of organic matter (prey mites or food for prey mites) decreased severity or speed of moulding. Addition of motile *Carpoglyphus lactis* mites (10% of total food) strongly reduced mycelium growth and therefore succeeded in keeping dead prey mites available to predation.

EXAMPLE 2

Setup

To immobilize prey mites, 7.5 g of *Carpoglypus lactis* was combined with 0.75 g of pure ethanol in 100 ml jars. Jars were closed and shaken to mix the contents. After 2, 3 or 4 hours at ambient temperatures, jars were opened again. To allow the material to breathe and to allow ethanol to evaporate, jars were closed with tops containing mesh. The jars were stored at 21° C. and 65-75% RH for the duration of the experiment. To monitor mite activity in respect of motility, samples of roughly 0.5 g were taken at different times after the ethanol treatment was started. From these samples motile mites were extracted using a modified berlese funnel and were counted.

Results

The results are presented in table 2.1 below.

TABLE 2.1

| hours after treament | treatment hours | adults | nymphs | larvae |
|---|---|---|---|---|
| 5 | 2 | 2.0 | 1.0 | 1.0 |
|  | 3 | 1.9 | 1.9 | 0.0 |
|  | 4 | 6.5 | 3.7 | 0.9 |

TABLE 2.1-continued

| hours after treament | treatment hours | adults | nymphs | larvae |
|---|---|---|---|---|
| 27 | 2 | 4.1 | 4.1 | 0.0 |
| | 3 | 0.0 | 4.1 | 0.0 |
| | 4 | 0.0 | 0.0 | 0.0 |
| 52 | 2 | 32.1 | 30.2 | 3.8 |
| | 3 | 13.8 | 11.8 | 11.8 |
| | 4 | 4.0 | 4.0 | 0.0 |
| 77 | 2 | 29.0 | 15.5 | 7.7 |
| | 3 | 25.8 | 31.3 | 20.3 |
| | 4 | 5.5 | 1.8 | 23.9 |
| 142 | 2 | 180.1 | 819.9 | 205.5 |
| | 3 | 228.4 | 325.3 | 76.1 |
| | 4 | 4.0 | 127.5 | 45.8 |
| 190 | 2 | 395.9 | 1165.3 | 516.3 |
| | 3 | 221.5 | 912.3 | 133.8 |
| | 4 | 224.3 | 1366.9 | 195.0 |

The table shows the number of mites that showed visible activity (per gram of medium at different moments after the ethanol was applied). Untreated material would result in roughly 15000 active individuals per gram (adults, nymphs and larvae combined). Two hours after applying ethanol most mites still showed activity, but mainly uncontrolled movements with their legs. After three hours of exposure to the ethanol the majority of mites were inactive. After 4 hours only few individuals showed only minor movements of the legs. After 1 day nearly all movement had ceased and only an occasional individual could be observed moving around. The first few days hardly any active mites were observed. Mites that were active in this period were of all life stages. After several days mite activity was slowly regained.

EXAMPLE 3

Setup

The acceptance of ethanol treated prey mites by predatory mites was tested in a choice experiment. A batch of *Carpoglyphus lactis* rearing was divided in three groups. One group (treatment E) received an ethanol treatment for three hours as described above. At the same time as the ethanol was applied, the second and third group was placed in a freezer at −18° C. After 18 hours both groups were taken out of the freezer. One group (treatment FE) was subjected to an additional ethanol treatment as described above, the other group (treatment F) received no further treatment. 27 hours after the treatment of the prey mites had started the produced material was used in a three-way-choice test with *A. limonicus*. Small portions of the prepared food were placed on three connected arenas and a number of *A. limonicus* was placed in the center. The following day the number of *A. limonicus* on each type of food was counted. The experiment was replicated 10 times.

Results

The results are presented in FIG. 5 as the average fraction of mites retrieved from the differently treated foods. Error bars display the SD. *A. limonicus* does not show a preference for the differently treated food (ANOVA, P=0.06) demonstrating that ethanol treated *Carpoglyphus lactis*, as a representative of *Astigmatid* mites, is equally acceptable as a food source in comparison to frozen *Carpoglyphus lactis*.

EXAMPLE 4

Setup

In this experiment exactly the same material from experiment 3 (treatments E, F and FE), was used. 27 hours after the treatment of the prey mites had started, the material was used to start a storage experiment at conditions similar to those used for rearing predatory mites. Small cups were filled with 0.6 g medium, five replicates per treatment. These were stored at 25° C. and 93% RH. The quality of the medium was assessed daily.

Results

Treatment E

After 2 days after cups were placed at 25° C. and 93% RH a few prey mites (ca. 1%) were active. The first fungal growth was observed on day 7 with 0-5 small mycelium patches per cup. At this time there were many prey mites active, about 20% of the initial number of mites before the ethanol treatment.

Treatment F

The first fungal growth was observed on day 3 with 3-6 small mycelium patches per cup. After 5 days 100% of the surface was covered by white mycelium. On day 7 green and yellow sporidia covered 70-100% and 5-20% of surface area respectively.

Treatment FE

The first fungal growth was observed on day 3 in some replicates with 0-1 small mycelium patches per cup. After 5 days 20% of the surface was covered by white mycelium. On day 7 the surface was entirely covered with white mycelium, and green and yellow sporidia covered 20-75% and 1% of surface area respectively.

As in the immobilization experiment (experiment 2), mites activity in the treatment E recovers after a few days. This treatment has by far the lowest development of fungus. This is believed to be caused by the recovering mites activity suppressing the fungus. In addition, the ethanol itself may reduce fungal growth. This is reflected by the fact that treatment FE has less fungal growth than treatment F, while in both treatments F and FE no active mites were observed.

EXAMPLE 5

Setup

Moulding data from rearing test involving a number of *Astigmatid* prey mites were evaluated in order to determine the fungus reducing effect of motile *Astigmatid* individuals. The data of rearings involving *Carpoglyphus lactis* (Cl), *Lepidoglyphus destructor* (Ld), *Suidasia pontifica* (Sp), *Thyreophagus entomophagus* (Te) and *Tyrophagus putrescentiae* (Tp) were collected and analyzed.

In the included tests rearing was performed as described in example 2. Moulding of medium was scored on the basis of mycelium clumping. The following scoring table was used: little (score 1), moderate (score 2) or severe (score 3).

Results

The dot plots presented in FIG. 6 show the moulding scores on bran and millet chaff (for Cl only) carrier in relation to prey mite densities for 5 species.

The fungus reducing effect of *Astigmatid* mites is apparent. Some mite species are more effective in suppression mould than others. *C. lactis* and *T. entomophagous*, for example are effective, under the tested conditions, at densities>500 mites/gram, whereas *L. destructor* and *S. pon-*

*tifica* need densities of >1000 mites/gram. The results also show that the chaff carrier is less prone to mould formation.

EXAMPLE 6

Setup

Rearing trials were setup for *A. swirskii* and *A. limonicus* as representatives of predatory mites of the family of the Phytoseiidae. *C. lactis* and *T. entomophagus* were selected as representatives of prey mites from the order Astigmata.

Rearing was performed in petridishes (Ø=25 mm, h=30 mm) with a ventilated lid of 90 um mesh nylon. These units were placed in a bigger container (l×w×h=33×20×15 cm) with a saturated salt solution on the bottom to create the desired humidity. All trials are performed at 85% RH, except those of *A. limonicus* (at 93% RH). The temperature was 25.0° C. (±0.3° C.) and the light regime 16/8 (L:D). The number of replicates per treatment was 3.

As carrier material for the mites, 10% moist wheat bran was used in all cases except for *A. limonicus* (here 13% moist millet chaff was used). The predatory mite rearing started out using the same inoculum at a relatively low density.

*Astigmatid* mites were reared on diets containing bran and yeast and supplied as food. The *Astigmatid* prey mites were offered to the predator in either live or live+frozen form depending on the test. The amount of frozen prey mites was twice the amount of live+frozen prey mites (except for *S. pontifica*, where the amount of frozen prey mites was 4 times the amount of live+frozen prey mites) in order to supply enough food but to maintain the ratio of live prey mites: predatory mites at acceptable levels (ratio<10, preferably 0-5). Carrier and prey were offered twice a week in an amount of 50% (w/w) of the inoculum. As a food source either immobilized (3-7 days at −18° C., defrosted 1 hour before use) *Astigmatid* individuals of selected species or a mixture of immobilized and live *Astigmatid* individuals of the selected species was presented. This made it possible to control the live:immobilized ratio (only for the live+frozen treatment). *Astigmatid* mites were reared on diets containing bran and yeast.

The trials lasted 18-50 days (see graphs) and twice a week 1 sample of each unit was taken. The live predatory mites and prey mites were extracted from this sample and counted. This way, the density (per gram) and ratio (live prey mites:live predatory mites) was calculated.

Results

The results are presented in FIG. 7 and show that the combination of live+immmobilized prey resulted in significant higher densities of Phytoseiid predator mites. For *A. swirskii* reared on *C. lactis* (panel A) the average increase was 150%, for *A. swirskii* reared on *T. entomophagus* (panel B) the increase was 135% and for *A. swirskii* reared on *S. pontifica* (panel C) the increase was 155%. For *A. limonicus* reared on *C. lactis* (panel D) this increase was the highest with 270%. The graphs show the density of predatory mites (per gram) (average±SE) during the course of the trial. Below the graph, the average per treatment and the p-value of the statistical test (two sample T-test comparing the averages) is presented.

It can be concluded that immobilized *Astigmatid* prey gives the mass-rearer the opportunity to feed higher quantities of *Astigmatid* prey mites, without the risk of increasing stress levels for the predator. This may result in significantly higher densities of predator mites and thus increase efficiency of mass-rearing.

EXAMPLE 7

Setup

Two species of predatory mites, *A. swirskii* and *A. limonicus*, were tested with respect to their preference for different carrier types. Mature females were collected approximately 10 days after the start of rearing from the egg stage. The 3 offered carriers were millet chaff, a carrier according to the invention, wheat bran, standard carrier and vermicullite (fine grain, all particles<2 mm), also a standard carrier. All carriers were simultaneously offered in a moist form (15 ml water/100 g added). Of each carrier 2 portions were placed opposite one another on a fixed distance from the release point (4 cm). The tested substrates were all offered in the same volume of 0.5 cc (divided in 2 portions per arena). At the start of the test, 10 females and 2 males of each species were placed in the middle of each plastic choice arena (Ø=12 cm). The arena was placed on moist cotton wool to offer water for the predatory mites and to prevent escape. *Typha* pollen was placed as a food source at the release point. The number of replicates was 3 and each subsequent arena was orientated with another substrate at top position (12 o'clock).

The test was performed in a climate room with conditions of 25° C., 75% RH and 16:8 (L:D) light regime and the RH on the arena was around 85%. After 2 days the number of predator eggs per substrate and the number of adults present were counted (male individuals were excluded from the statistics). For this all carrier particles were scrutinized individually and also checked 2 days later after extra food was added. The results per substrate per species were statistically analysed using the Chi-square Goodness of Fit Test (one variable).

Results

The total number of females found in each substrate (after 3 replicates) is presented in FIG. 8 (panel A). Of all start-up females (30) a large fraction of individuals was retrieved from the substrates, i.e. 87% (26 individuals) of all *A. limonicus* and 60% (18 individuals) of all *A. swirskii*. Thus even though the material was clearly separated from the food source, the majority of female mites were found in this carrier. Both tests showed a significant difference between carrier materials (p=0.000).

The total number of eggs (and hatchlings) found in each carrier (after 3 replicates) is shown in panel B of FIG. 1. It is clear that the occurrence of female mites correlates with the number of eggs laid on the carriers. Both tests showed a significant difference between carrier materials (p=0.000).

The results indicate that carrier materials providing mite shelters, as represented by the millet chaff in this experiment, are a highly preferred for mite species, such as Phytoseiid species.

EXAMPLE 8

Setup

Thick layers of medium were prepared to simulate a mass-rearing unit. Either bran or millet chaff (both moistened) were used as the carrier material. Bran is the standard carrier used in commercial mite rearing. Chaff is a representative for carriers according to the invention with mite shelters. Two food types (A and B), both comprising *C. lactis* in frozen form were used. In a start-up rearing the predatory mite, *A. limonicus*, was reared for >2 generations on the test medium layers. The subsequent rearing was performed in layers of 6-7 cm high in ventilated boxes (L×W×H=15×15×8 cm) during 2 weeks. Sampling, feeding and mixing was done twice a week. The test was performed in duplo at 21° C. and 93% RH. Each week the number of live predator and prey mites were counted from the sample.

Results

The results are presented in FIG. 9. The predator densities in the chaff rearings are increasing in the first and second week, on both food types. In the bran mixes, the rearings are keeping up in the first week, but collapse in the second week. The decrease of predator numbers is followed by an increase of prey mite numbers and this makes continuity of these rearing mixes troublesome. The test shows a net result that is positive for the chaff carrier as compared to the standard bran carrier.

REFERENCES

Solomon, M. E. and Cunnington, A. M., 1963, Rearing acaroid mites, Agricultural Research Council, Pest Infestation Laboratory, Slough, England, pp 399-403.

Parkinson, C. L., 1992, "Culturing free-living astigmatid mites." Arachnida: Proceedings of a one day symposium on spiders and their allies held on Saturday 21 Nov. 1987 at the Zoological Society of London, eds. Cooper, J. E., Pearce-Kelly, P, Williams, D. L., p. 62-70.

Hughes, A. M., 1977, The mites of stored food and houses. Ministry of Agriculture, Fisheries and Food, Technical Bulletin No. 9: 400 pp De Moraes, G. J., McMurtry, J. A., Denmark, H. A. & Campos, C. B., 2004. A revised catalog of the mite family Phytoseiidae. Magnolia Press Auckland New Zealand 494 pp.

The invention claimed is:

1. A mite composition comprising:
   a population of individuals of a predatory mite species selected from *Mesostigmatid* mite species or *Prostigmatid* mite species;
   a food source for the population of individuals of the predatory mite species, wherein the food source comprises individuals of at least one *Astigmatid* mite species, wherein at least a fraction of the *Astigmatid* individuals is immobilized by an immobilization treatment;
   wherein the immobilized *Astigmatid* individuals are contacted with a fungus reducing agent comprising a fungus reducing mite population selected from a mycophagous mite species or an antifungal exudates producing mite species.

2. The composition according to claim 1, wherein the predatory mite species is selected from:
   *Mesostigmatid* mite species selected from:
      i) *Phytoseiidae*;
      ii) *Ascidae*;
      iii) *Laelapidae*;
      iv) *Macrochelidae*;
      v) *Parasitidae*; and
   *Prostigmatid* mite species such as selected from:
      vi) *Tydeidae*;
      vii) *Cheyletidae*;
      viii) *Cunaxidae*;
      ix) *Erythraeidae*; and
      x) *Stigmaeidae*.

3. The composition according to claim 1, wherein the at least one *Astigmatid* mite species comprises a species selected from:
   i) *Carpoglyphidae*;
   ii) *Pyroglyphidae*;
   iii) *Glycyphagidae*;
   iv) *Acaridae*; and
   v) *Suidasiidae*.

4. The composition according to claim 1, wherein the ratio of predatory individuals relative to *Astigmatid* individuals is from about 100:1 to 1:100.

5. The composition according to claim 1, comprising a carrier and containing ≥10 up to 450 individuals per ml carrier.

6. The composition according to claim 1, wherein the fraction of immobilized *Astigmatid* individuals is ≥10%.

7. The composition according to claim 1, wherein the immobilization treatment is selected from thermal treatment; chemical treatment; by radiation treatment; by mechanical treatment; by electrical treatment; immobilisation with an adhesive; or immobilisation by starvation.

8. The composition according to claim 1, further comprising a food substance suitable for *Astigmatid* individuals, and said food substance for *Astigmatid* individuals is contacted with the fungus reducing agent comprising a fungus reducing mite population selected from a mycophagous mite species or an antifungal exudates producing mite species.

9. The composition according to claim 1, further comprising a carrier for the individuals of the mite species.

10. The composition according to claim 9, wherein the carrier for the individuals of the mite species comprises carrier elements and wherein the stacking of the carrier elements comprises shelters suitable for predatory mite individuals.

11. The composition according to claim 10, wherein the shelters comprise areas where the material of the carrier element shields a predatory individual, when located in this area, from its surroundings in at least 3 directions having orthogonal or reversed relations.

12. The composition according to claim 10, wherein the shelters comprise voids.

13. The composition according to claim 10, wherein carrier elements are derived from chaff.

14. The composition according to claim 1, further comprising a food substance suitable for *Astigmatid* individuals and a carrier for the individuals of the mite species, wherein said food substance for *Astigmatid* individuals is contacted with the fungus reducing agent comprising a fungus reducing mite population selected from a mycophagous mite species or an antifungal exudates producing mite species.

15. The composition according to claim 1, wherein the immobilized fraction of the *Astigmatid* individuals comprises one or more of larvae, nymphs and adults.

16. The composition according to claim 1, wherein when the predatory mite species is selected from:
   i) *Phytoseiidae* it is selected from the subfamily of the Amblyseiinae or Typhlodrominae;
   ii) *Ascidae* it is selected from the genus *Proctolaelaps, Blattisocius, Lasioseius, Arctoseius*, or *Protogamasellus*;
   iii) *Laelapidae* it is selected from the genus *Stratiolaelaps, Geolaelaps*, or *Androlaelaps*;
   iv) *Macrochelidae* it is selected from the genus *Macrocheles*;
   v) *Parasitidae* it is selected from the genus *Pergamasus*; and
   vi) *Tydeidae* it is selected from the genus *Homeopronematus, Tydeus*, or *Pronematus*;
   vii) *Cheyletidae* it is selected from the genus *Cheyletus*;
   viii) *Cunaxidae* it is selected from the genus *Coleoscirus* or *Cunaxa*;
   ix) *Erythraeidae* it is selected from the genus *Balaustium*; and x) *Stigmaeidae* it is selected from the genus *Agistemus* or *Zetzellia*.

17. The composition according to claim 16, wherein when the predatory mite species is selected from:
the subfamily of the Amblyseiinae, it is selected from the genus *Amblyseius, Euseius, Neoseiulus, Amblydromalus, Typhlodromalus, Typhlodromips*, or *Phytoseiulus*; and
the subfamily of the Typhlodrominae, it is selected from the genus *Galendromus* or *Typhlodromus*.

18. The composition according to claim 1, wherein when the at least one *Astigmatid* mite species is:
  i) *Carpoglyphidae* it is *Carpoglyphus lactis;*
  ii) *Pyroglyphidae* it is selected from the genus *Dermatophagoides*, or *Pyroglyphus;*
  iii) *Glycyphagidae* it is selected from the genus *Diamesoglyphus, Ctenoglyphus, Blomia, Glycyphagus, Lepidoglyphus, Austroglycyphagus, Aëroglyphus, Gohieria, Coproglyphus, Chortoglyphus , Glycyphagus* or *Lepidoglyphus;*
  iv) *Acaridae* it is selected from the genus *Tyrophagus, Acarus, Thyreophagus*, or *Aleuroglyphus;* and
  v) *Suidasiidae* it is from the genus *Suidasia*.

19. A method for rearing a predatory mite species, the method comprising:
  (i) providing a composition according to claim 1;
  (ii) allowing individuals of the predatory mite population to prey on individuals of the *Astigmatid* population.

20. A method comprising:
applying a composition according to claim 1 to a field crop.

* * * * *